United States Patent
Meyer-Lueckel et al.

(10) Patent No.: US 8,853,297 B2
(45) Date of Patent: *Oct. 7, 2014

(54) METHOD AND MEANS FOR INFILTRATING ENAMEL LESIONS

(75) Inventors: Hendrik Meyer-Lueckel, Langwedel (DE); Sebastian Paris, Osdorf (DE); Jan Mueller, Konigs-Wusterhausen (DE); Andrej M. Kielbassa, Berlin (DE); Bernd Detje, Hamburg (DE)

(73) Assignees: Charite Universitatsmedizin Berlin, Berlin (DE); Muhlbauer Technology GmbH, Hamburg (DE)

( * ) Notice: Subject to any disclaimer, the term of this patent is extended or adjusted under 35 U.S.C. 154(b) by 749 days.

This patent is subject to a terminal disclaimer.

(21) Appl. No.: 12/300,437
(22) PCT Filed: May 11, 2007
(86) PCT No.: PCT/EP2007/004204
§ 371 (c)(1), (2), (4) Date: Jun. 19, 2009
(87) PCT Pub. No.: WO2007/131725
PCT Pub. Date: Nov. 22, 2007

(65) Prior Publication Data
US 2009/0304622 A1 Dec. 10, 2009

Related U.S. Application Data

(63) Continuation of application No. 11/432,271, filed on May 11, 2006.

(30) Foreign Application Priority Data

Oct. 19, 2006 (EP) ..................................... 06021966

(51) Int. Cl.
| | |
|---|---|
| A61K 6/083 | (2006.01) |
| C08L 33/00 | (2006.01) |
| C08L 33/10 | (2006.01) |
| G01N 11/02 | (2006.01) |

(52) U.S. Cl.
CPC ..................................... *A61K 6/083* (2013.01)
USPC ........... 523/115; 523/113; 523/118; 424/666; 424/78.31

(58) Field of Classification Search
USPC .......................................................... 523/115
See application file for complete search history.

(56) References Cited

U.S. PATENT DOCUMENTS 2,565,569 A * 8/1951 McCants ....................... 549/352
4,182,035 A * 1/1980 Yamauchi et al. .......... 433/228.1
(Continued)

FOREIGN PATENT DOCUMENTS

| | | |
|---|---|---|
| EP | 06021966.4 | 10/2006 |
| WO | WO 00/09030 | 2/2000 |
| WO | WO 2007/131725 | 11/2007 |

OTHER PUBLICATIONS

Buckton, G. "Interfacial phenomena in drug delivery and targeting" Chur, 1995 vol. 289 pp. 207,8.

(Continued)

*Primary Examiner* — James J Seidleck
*Assistant Examiner* — Peter A Salamon
(74) *Attorney, Agent, or Firm* — Casimir Jones S.C.

(57) ABSTRACT

The present invention refers to a method of infiltrating enamel for the prevention and/or treatment of carious lesions comprising (a) exposing an enamel area to a conditioner comprising hydrochloric acid; (b) exposing the conditioned enamel area to an infiltrant; and (c) curing the infiltrant. The present invention further refers to a kit for carrying out the method of infiltrating enamel, which comprises a conditioner comprising hydrochloric acid and an infiltrant comprising at least one low viscous dental resin. Alternatively, the kit comprises ready-to-use means for carrying out the method of infiltrating enamel, e.g. application strips with delivery pads soaked with conditioner or infiltrant. The present invention also refers to a method for identifying an infiltrant by calculation of the penetration coefficient, and to an infiltrant identified by the method having a penetration coefficient of >50 cm/s or comprising a low viscous light curing resin having a penetration coefficient of >50 cm/s.

21 Claims, 13 Drawing Sheets

(56) References Cited

U.S. PATENT DOCUMENTS

| | | | | |
|---|---|---|---|---|
| 4,515,910 | A * | 5/1985 | Rawls et al. | 523/115 |
| 4,719,149 | A * | 1/1988 | Aasen et al. | 428/473 |
| 5,277,739 | A * | 1/1994 | Muller et al. | 156/330.9 |
| 5,866,629 | A * | 2/1999 | Santerre et al. | 523/118 |
| 5,922,786 | A * | 7/1999 | Mitra et al. | 523/118 |
| 6,072,086 | A * | 6/2000 | James et al. | 568/449 |
| 6,729,879 | B2 * | 5/2004 | Allred et al. | 433/226 |
| 6,756,417 | B2 * | 6/2004 | Allred et al. | 522/13 |
| 6,916,858 | B2 * | 7/2005 | Kojima et al. | 523/118 |
| 2003/0130427 | A1 * | 7/2003 | Cleary et al. | 525/192 |
| 2003/0157034 | A1 * | 8/2003 | Jia et al. | 424/49 |
| 2003/0162864 | A1 * | 8/2003 | Pearson et al. | 523/115 |
| 2004/0229973 | A1 * | 11/2004 | Sang et al. | 523/118 |
| 2006/0167129 | A1 * | 7/2006 | Meyer-Lueckel et al. | 523/115 |
| 2006/0264532 | A1 * | 11/2006 | Meyer-Lueckel et al. | 523/115 |
| 2009/0304622 | A1 * | 12/2009 | Meyer-Lueckel et al. | 424/78.31 |

OTHER PUBLICATIONS

Davila, et al. "Adhesive penetration in human artificial and natural white spots" J Dent Res. Sep.-Oct. 1975;54(5):999-1008.

De Araujo, et al. "Diagnosis of approximal caries: radiographic versus clinical examination using tooth separation" Am J Dent, 1992, 5:245-248.

Fan, et al. "Penetrativity of sealants" J Dent Res. Mar.-Apr. 1975;54(2):262-4.

Garcia-Godoy, et al. "Caries progression of white spot lesions sealed with an unfilled resin" J Clin Pediatr Dent. 1997 Winter;21(2):141-3.

Gray, et al. "Infiltration of resin into white spot caries-like lesions of enamel: an in vitro study" Eur J Prosthodont Restor Dent. Mar. 2002;10(1):27-32.

Irinoda, et al. "Effect of sealant viscosity on the penetration of resin into etched human enamel" Oper Dent. Jul.-Aug. 2000;25(4):274-82.

Kogon, et al. "Can radiographic criteria be used to distinguish between cavitated and noncavitated approximal enamel caries?" Dentomaillofac Radiol, 1987, 16:33-36.

Marthaler, et al. "Radiographic and visual appearance of small smooth surface caries lesions studied on extracted teeth" Caries Res, 1970, 4:224-242.

Martignon, et al. "Efficacy of sealing proximal early active lesions: an 18-month clinical study evaluated by conventional and subtraction radiography" Caries Res. 2006;40(5):382-8.

Mejare, et al. "Caries development from 11 to 22 years of age: a prospective radiographic study. Prevalence and distribution" Caries Res. 1998;32(1):10-6.

Meyer-Lueckel, et al. "Influence of the application time on the penetration of different dental adhesives and a fissure sealant into artificial subsurface lesions in bovine enamel" Dent Mater. Jan. 2006;22(1):22-8.

Mueller, et al. "Inhibition of lesion progression by penetration of resins in vitro: Influence of the application procedure" Oper Dent 2006, 31:338-345.

Paris, et al. "Progression of sealed initial bovine enamel lesions under demineralizing conditions in vitro" Caries Res. 2006;40(2):124-9.

Ratledge, et al. "A clinical and microbiological study of approximal carious lesions. Part 1: The relationship between cavitation, radiographic lesion depth, the site-specific gingival index and the level of infection of the dentine" Caries Res, 2001, 35:3-7.

Robinson, et al. "Arrest and control of carious lesions: a study based on preliminary experiments with resorcinol-formaldehyde resin" J Dent Res. Sep.-Oct. 1976;55(5):812-8.

Robinson, et al. "In vitro studies of the penetration of adhesive resins into artificial caries-like lesions" Caries Res. Mar.-Apr. 2001;35(2):136-41.

Rugg-Gunn, AJ. "Approximal carious lesions. A comparison of the radiological and clinical appearances" Br Dent J, 1972, 133:481-484.

Schmidlin, et al. "Penetration of a bonding agent into De- and remineralized enamel in vitro" J Adhes Dent. 2004 Summer;6(2):111-5.

Olin et al. "Enamel surface modification in vitro using hydrochloric acid pumice: an SEM investigation," Quintessence International, 18(10): 733-736, 1988.

Asmussen et al. "Penetration of restorative resins into acid etched enamel. I. Viscosity, surface tension and contact angle of restorative resin monomers," Acta Odont. Scand, 35:175-182, 1977.

* cited by examiner

METHOD AND MEANS FOR INFILTRATING ENAMEL LESIONS

This application is a §371 U.S. National Entry of International Application No. PCT/EP2007/004204, filed May 11, 2007, which is a Continuation-in-Part of U.S. Application Ser. No. 11/432,271, filed May 11, 2006, and which claims the benefit of European Application No. 06 021 966.4, filed Oct. 19, 2006.

The present invention refers to a method for identifying an infiltrant by calculation of the penetration coefficient, and to infiltrants for low viscous dental resins having a penetration coefficient of >50 cm/s. The present invention refers to a use of said infiltrants for infiltrating enamel, in particular for the prevention and/or treatment of carious lesions. The present invention further refers to a kit for infiltrating enamel, which kit comprises a conditioner comprising hydrochloric acid and an infiltrant comprising at least one low viscous dental resin. The present invention also refers to a kit for infiltrating enamel, which kit comprises ready-to-use application strips and, optionally, cleaning strips and a teeth separating means.

BACKGROUND OF THE INVENTION

In industrial countries, about 98% of the adult population exhibits one or more carious lesions or are already provided with fillings. Any carious lesion which eventually may lead to cavitation is initiated by demineralization of the hard tooth substance. At an early stage, referred to as "initial enamel caries", the tooth surface remains intact without visible signs of erosion but the demineralized area below the surface becomes more and more porous.

Today, the only non-operative ways to treat approximal caries are to enhance remineralization by application of fluorides and to arrest lesion progress by improvement of patient's oral hygiene. While smooth surfaces of the tooth are more susceptible for improved cleaning strategies, approximal surfaces are particularly difficult to clean. Nevertheless, remineralization in approximal lesions that have reached the dentin seems to be hardly achievable, since several clinical studies showed that from this threshold a visible cavitation of the lesion is established in most cases (Rugg-Gunn A J. Approximal carious lesions. A comparison of the radiological and clinical appearances. *Br Dent J*, 1972, 133:481-484; De Araujo F B et al. Diagnosis of approximal caries: radiographic versus clinical examination using tooth separation. *Am J Dent*, 1992, 5:245-248; Ratledge et al. A clinical and microbiological study of approximal carious lesions. Part 1: The relationship between cavitation, radiographic lesion depth, the site-specific gingival index and the level of infection of the dentine. *Caries Res*, 2001, 35:3-7). Moreover, in vitro studies even found many cavitations in lesions confined to enamel. A cavitated enamel lesion cannot be cleaned sufficiently by the patient and will progress (Marthaler T M and Germann M. Radiographic and visual appearance of small smooth surface caries lesions studied on extracted teeth. *Caries Res*, 1970, 4:224-242; Kogon S L et al. Can radiographic criteria be used to distinguish between cavitated and noncavitated approximal enamel caries? *Dentomaillofac Radiol*, 1987, 16:33-36). Therefore, if a cavitation occurs even at such an early stage of the caries process, a remineralization seems very unlikely under clinical conditions. This could explain clinical findings, that fluoridation and improved oral hygiene can only slow down the progression of approximal caries but are not capable of reversing it (Mejare I et al. Caries development from 11 to 22 years of age: A prospective radiographic study. Prevalence and distribution. *Caris Res*, 1998, 32:10-16).

Once a cavitation has developed, invasive methods of treatment are generally indicated. However, drilling out carious tooth material is always accompanied by the removal of non-carious, i.e. sound, hard tooth substance. In approximal carious lesions which are difficult to reach, the ratio of carious and intact substance being removed is particularly unfavorable. Moreover, the connection between an inserted filling and the endogenous tooth material is susceptible for carious lesions itself, and renewal of fillings due to the ageing process leads to further removal of sound tooth material. Therefore, methods of treating caries at an early stage, and in particular approximal initial carious lesions, are highly desirable in order to prevent later requirement for invasive procedures.

One apparent indication of initial enamel caries are white spot lesions. Such a lesion is characterized by a loss of mineral in the bulk of enamel, whereas the surface of the lesion remains relatively intact (so-called "pseudo-intact surface layer"). A promising approach of non-operative dentistry might be the sealing of enamel lesions with low viscous light curing resins such as dental adhesives and fissure sealants. The tiny pores within the lesion body act as diffusion pathways for acids and dissolved minerals and, therefore, enable the dissolution of enamel at the advancing front of the lesion. The aim of the proposed regimen is not only to seal the surface but to infiltrate these pores, thereby withdrawing the lesion body from further attack. Moreover, after curing the resin material, a mechanical support of the fragile enamel framework in the lesion will be achieved. Therefore, an occlusion of the pores by infiltration with light curing resins might arrest the lesion progression and mechanically stabilize the fragile lesion structure.

The idea to arrest caries by sealing with low viscous resins has been followed in several in vitro experiments since the seventies of the last century (Robinson C et al. Arrest and control of carious lesions: A study based on preliminary experiments with resorcinol-formaldehyde resin. *J Dent Res*, 1976, 55:812-818; Davila J M et al. Adhesive penetration in human artificial and natural white spots. *J Dent Res*, 1975, 54:999-1008; Gray G B and Shellis P. Infiltration of resin into white spot caries-like lesions of enamel: An in vitro study. *Eur J Prosthodont Restor Dent*, 2002, 10:27-32; Garcia-Godoy F et al. Caries progression of white spot lesions sealed with an unfilled resin. *J Clin Pediatr Dent*, 1997, 21:141-143; Robinson C et al. In vitro studies of the penetration of adhesive resins into artificial caries-like lesions. *Caries Res*, 2001, 35:136-141; Schmidlin P R et al. Penetration of a bonding agent into de- and remineralized enamel in vitro. *J Adhes Dent*, 2004, 6:111-115). It could be shown that sealants can penetrate the body of artificial lesions nearly completely (Gray G B and Shellis P. Infiltration of resin into white spot caries-like lesions of enamel: An in vitro study. *Eur J Prosthodont Restor Dent*, 2002, 10:27-32; Meyer-Lueckel, H et al. Influence of the application time on the penetration of different adhesives and a fissure sealant into artificial subsurface lesions in bovine enamel. *Dent Mater* 2006, 22:22-28), and reduce the accessible pore volumes within the lesions significantly (Robinson C et al. In vitro studies of the penetration of adhesive resins into artificial caries-like lesions. *Caries Res*, 2001, 35:136-141). Moreover, it has been observed that sealants are capable to inhibit further lesion progress under demineralizing conditions (Robinson C et al. Arrest and control of carious lesions: A study based on preliminary experiments with resorcinol-formaldehyde resin. *J Dent Res*, 1976, 55:812-818; Garcia-Godoy F et al. Caries progression of whit spot lesions sealed with an unfilled resin. *J Clin Pediatr Dent*, 1997, 21:141 - 143; Robinson et al. In vitro studies of the penetration of adhesive resins into artificial caries-like lesions. *Caries Res*, 2001, 35:136-141; Muller J et al. Inhibition of lesion progression by penetration of resins in vitro: Influence of the application procedure. *Oper Dent* 2006, 31:338-345; Paris S et al. Progression of sealed initial bovine enamel lesions under demineralizing conditions in vitro. *Caries Res*, 2006, 40:124-129).

However, one of the problems in sealing natural enamel lesions is that "pseudo-intact surface layers" have higher mineral contents compared to carious bodies of lesion. As a consequence, these layers inhibit the penetration of the lesion body by the sealing material and may even function as a barrier. In the end, the surface layer may be superficially sealed, but the carious body may be insufficiently penetrated by the resin. At worst, the carious process further proceeds below the "seal".

Efforts have been made to enhance the penetration of sealants in enamel lesions. In an in vitro model, artificial enamel lesions were produced showing an intact surface layer, a body of lesion and a progressive demineralization front. It has been shown that a 5 seconds etching of those artificially induced lesions with phosphoric acid resulted in deeper penetration depths (Gray G B and Shellis P. Infiltration of resin into white spot caries-like lesions of enamel: An in vitro study. *Eur Prosthodont Restor Dent*, 2002, 10:27-32). Thus, such a pretreatment or "conditioning" of an enamel area by etching could also improve the penetration of sealant in vivo. However, artificially induced enamel lesions differ from natural lesions in that they comprise regular and relatively thin "pseudo-intact surface layers". Natural enamel lesions, in contrast, usually show higher mineralized surface layers of varying thickness. Thus, conditioning with phosphoric acid, although demonstrated as successful in vitro, must not necessarily provide for a benefit in vivo.

WO 00/09030 discloses a teeth-coating method that protects teeth from caries and peridontal diseases along with giving color to them. This coating method consists of the steps of (a) etching the teeth, for example by acid or laser; (b) application of a protective substance to the etched teeth; and (c) sealing the teeth. For acid etching, commonly employed materials such as phosphoric acid, maleic acid, citric acid and pyruvic acid are mentioned.

Nevertheless, an in vivo study reported that the application of a conventional adhesive onto enamel lesions pre-treated with phosphoric acid gel resulted in retardation of caries progression compared to controls (Martignon et al. *Caries Res*, 2006, 40:382-388). However, patients were monitored for two years only and diagnosis was done by X-raying, a rather insensitive method for analyzing successful penetration. Therefore, the results of this study should be regarded with some caution, as even the authors concede. Moreover, it remains unclear whether this initial success would be seen after longer periods since the rather superficial "seal" might be destroyed due to the physical load in vivo.

In the previous studies only commercially available adhesives and fissure sealants which have been optimized for adhesive purposes have been used to penetrate subsurface enamel lesions. Composite resins optimized to rapidly infiltrate these enamel lesions ("infiltrants") might achieve better sealing results. In order to develop such composite resins, a better understanding of the processes occurring during the penetration of enamel lesions is needed.

Physically, the penetration of a liquid (uncured resin) into a porous solid (enamel lesion) is described by the Washburn equation (Equation 1, see below). This equation assumes that the porous solid is a bundle of open capillaries (Buckton G. Interfacial phenomena in drug delivery and targeting. Chur, 1995); in this case, the penetration of the liquid is driven by capillary forces.

$$d^2 = \left(\frac{\gamma \cdot \cos\theta}{2\eta}\right) r \cdot t \qquad \text{-Equation 1-}$$

d distance, moved by the liquid resin
γ surface tension of the liquid resin (to air)
θ contact angle of the liquid resin (to enamel)
η dynamic viscosity of the liquid resin
r capillary (pore) radius
t penetration time The bracketed term of the Washburn equation is the penetration coefficient (PC, Equation 2, see below) (Fan P L et al. Penetrativity of sealants. *J Dent Res*, 1975, 54:262-264). The PC is composed of the liquid's surface tension to air (γ), the cosine of the liquid's contact angle to enamel (θ) and the dynamic viscosity of the liquid (η). The higher the coefficient is, the faster the liquid penetrates a given capillary or porous bed. This means that a high PC can be achieved for high surface tensions, low viscosities and low contact angles where the influence of the contact angle is comparatively low.

$$PC = \left(\frac{\gamma \cdot \cos\theta}{2\eta}\right) \qquad \text{-Equation 2-}$$

PC penetration coefficient
γ surface tension of the liquid resin (to air)
θ contact angle of the liquid resin (to enamel)
η dynamic viscosity of the liquid resin Previously, a positive correlation between the penetration coefficients (PCs) of commercial sealants and their ability to penetrate into fissures could be found (O'Brien W J et al. Penetrativity of sealants and glazes. The effectiveness of a sealant depends on its ability to penetrate into fissures. *Oper Dent*, 1987, 3:51-56). Moreover, low viscouse sealants showed deeper penetration when applied on etched enamel (Irinoda Y et al. Effect of sealant viscosity on the penetration of resin into etched human enamel. *Oper Dent* 2000, 25:274-282). However, no study has hitherto focused on the influence of the PC on resin penetration into carious lesions. The penetration of five commercially available adhesives and one fissure sealant into artificial enamel lesions was subject of a recent study (Meyer-Lueckel, H et al. Influence of the application time on the penetration of different adhesives and a fissure sealant into artificial subsurface lesions in bovine enamel. *Dent Mater*, 2006, 22:22-28). The penetration depth was shown to depend on penetration time. In this study, the best performing commercially available material Excite® penetrated 105 μm in 30 seconds and completely filled artificial enamel lesions. The square correlation between penetrated depth and time arising from the Washburn equation (see Equation 1) showed that enormous penetration times are needed if a deep infiltration of natural lesion (>1000 μm) is aimed with commercially available materials. This underlines the need for faster penetration composites. However, application times of more than 120 seconds are hardly acceptable for use in a dentist's daily practice due to economical reasons.

Thus, there is still a strong need for improved non-operative procedures of treating initial or even advanced enamel lesions in order to inhibit caries progression.

It is therefore an object of the present invention to provide for methods and means enabling improved resin penetration of initial or advanced enamel lesions.

SUMMARY OF THE INVENTION

The object of the present invention is solved by a method for identifying an infiltrant for infiltrating enamel having a penetration coefficient of >50 cm/s or comprising a low viscous light curing resin having a penetration coefficient of >50 cm/s, using the following equation:

$$PC = \left(\frac{\gamma \cdot \cos\theta}{2\eta}\right) \qquad \text{-Equation 2-}$$

wherein:
PC refers to the penetration coefficient;
γ refers to the surface tension of the liquid resin (to air);
θ refers to the contact angle of the liquid resin (to enamel); and
η refers to dynamic viscosity of the liquid resin.

In one embodiment, the method comprises:
(a) providing a potential infiltrant;
(b) determining the characteristics of contact angle, surface tension, and dynamic viscosity exhibited by the potential infiltrant; and
(c) determining the potential infiltrant's penetration coefficient by applying Equation 2 to the determined characteristics of (b).

In one embodiment, the method further comprises:
(d) selecting the potential infiltrant if it has a penetration coefficient of >50 cm/s.

In a preferred embodiment of the method, the selecting in (d) comprising separating the potential infiltrant from other potential infiltrants having a penetration coefficient of <50 cm/s.

In an alternative embodiment, the method further comprises:
(d) evaluating the hardening capacity of the potential infiltrant.

In another alternative embodiment, the method comprises:
(d) assessing the potential infiltrant's consistency after curing.

In just another alternative embodiment, the method comprises:
(d) determining the penetration quotient of the potential infiltrant.

The object of the present invention is further solved by an infiltrant identified using the method according to the present invention for identifying an infiltrant having a penetration coefficient of >50 cm/s or comprising a low viscous light curing resin having a penetration coefficient of >50 cm/s using the following equation:

$$PC = \left(\frac{\gamma \cdot \cos\theta}{2\eta}\right) \qquad \text{-Equation 2-}$$

wherein:
PC refers to the penetration coefficient;
γ refers to the surface tension of the liquid resin (to air);
θ refers to the contact angle of the liquid resin (to enamel);
η refers to dynamic viscosity of the liquid resin.

The object of the present invention is further solved by an infiltrant comprising at least one low viscous resin selected from the group of bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl)triclodecane; BEMA, benzyl methacrylate; SIMA, 3-trimethoxysilane propylmethacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In one embodiment, the infiltrant further comprises additives selected from the group comprising CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Methylenebis(6-t-butyl-4-ethylphenol); BPE, benzoic acid phenylester; MMMA methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

In one embodiment, the infiltrant has a penetration coefficient of >50 cm/s or comprising a low viscous light curing resin having a penetration coefficient of >50 cm/s.

The object of the present invention is also solved by an infiltrant comprising at least one resin or low viscous resin, preferably selected from the group comprising dental composite resins, dental adhesive resins and/or fissure sealant resins, wherein the infiltrant has a penetration coefficient of >50 cm/s or comprising a low viscous light curing resin having a penetration coefficient of >50 cm/s.

In one embodiment of the infiltrant, the resin is selected from the group comprising methacrylates and/or dimethacrylates and/or trimethacrylates, preferably selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propylmethacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a preferred embodiment, the methacrylates comprises monomers carrying an acid group, preferably a carboxyl, phosphonic, phosphoric, sulfonic or boric acid group. One such example is MDP, 10-methacryloyldecyldihydrogen phosphate.

In a preferred embodiment, the infiltrant further comprises one or more additives for curing.

The additives can be combined such that one-component infiltrants or two-component infiltrants are prepared. The additives can provide for light-curing and/or self-curing infiltrants.

In a more preferred embodiment, the additive is selected from the group comprising CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

These additives provide for light-curing infiltrants.

In an alternatively preferred embodiment, the additive is selected from the group comprising organic acids or salts thereof, preferably selected from the group comprising sulfinic acids and salts thereof, barbituric acids and salts thereof, and barbituric acid derivatives.

Examples of sulfinic acid salts are alkali metal salts, such as lithium, sodium or poassiuim salts; earth alkali metal salts, such as magnesium, calcium, strontium or barium salts; amine salts, such as primary amine salts having e.g. a methylamine, ethylamine, propylamine, butylamine, aniline, toluidine, phenyldiamin or xylylendiamin group, secondary amine salt having e.g. a dimethylamine, diethylamine, dipropylamine, dibutylamine, piperidine, N-methylaniline, N-ethylaniline, diphenylamine or N-methyltoluidine group, and tertiary amine salts having a trimethylamine, triethylamine, pyridine, N,N-dimethylaniline, N,N-di(beta-hydroxyethyl)aniline, N,N-diethylamine, N,N-dimethyltoluidine, N,N-diethyltoluidin or N,N-(beta-hydroxethyl)toluidin group, or ammonium salts, such as tetramethyl ammonium, tetraethyl ammonium, tetrapropyl ammonium or trimethylbezyl ammonium salts.

In a more preferred embodiment, the sulfinic acid is selected from the group comprising alkane sulfinic acids, alicyclic sulfinic acids and aromatic sulfinic acids In a particularly preferred embodiment, the alkane sulfinic acid is selected from the group comprising ethane sulfinic acid, propane sulfinic acid, hexane sulfinic acid, octane sulfinic acid, decane sulfinic acid, and dodecane sulfinic acid.

In another particularly preferred embodiment, the alicyclic sulfinic acid is cyclohexane or cyclooctane sulfinic acid.

In just another particularly preferred embodiment, the aromatic sulfinic acid is selected from the group comprising benzene sulfinic acid, o-toluene sulfinic acid, p-toluene sulfinic acid, ethylbenzene sulfinic acid, decylbenzene sulfinic acid, dodecylbenzene sulfinic acid, chlorobenzene sulfinic acid, and naphthalene sulfinic acid.

Examples of benzene sulfinic acid salts are sodium, potassium, magnesium, calcium, strontium, barium, butylamine, aniline, toluidine, phenylendiamine, diethylamine, diphenylamine, triethylamine, ammonium, tetramethylammonium, and trimethylbenzylammonium salts.

Examples of o-toluene sulfinic acid salts are lithium, sodium, potassium, calcium, cyclohexylamine, aniline, ammonium, and tetraethylammonium salts.

Examples of p-toluene sulfinic acid salts are lithium, sodium, potassium, calcium, barium, ethylamine, toluidine, N-methylaniline, pyridine, ammonium, and tetramethylammonium salts.

Examples of beta-naphtalene sulfinic acid salts are sodium, strontium, triethylamin, N-methyltoluidine, ammonium, and trimethylbenzylammonium salts.

Most particularly preferred aromatic sulfinic acid salts are sodium benzene sulfinate and sodium toluene sulfinate.

In a more preferred embodiment, the barbituric acid is selected from the group comprising 1,3,5-trimethyl barbituric acid, 1,3,5-triethylbarbituric acid, 1,3-dimethyl-5-ethyl barbituric acid, 1,5-dimethyl barbituric acid, 1-methyl-5-ethyl barbituric acid, 1-methyl-5-propyl barbituric acid, 5-ethyl barbituric acid, 5-propyl barbituric acid, 5-butyl barbituric acid, 5-methyl-1-butyl barbituric acid, 1-benzyl-5-phenyl barbituric acid, and 1-cyclohexyl-5-ethyl barbituric acid. Further considered are alkali metal salts of these barbituric acids.

In a further alternatively preferred embodiment, the additive is selected from the group comprising persulfates and organic peroxides.

Persulfates and peroxides are preferably admixed to the infiltrant prior to use of the infiltrant.

Examples of organic peroxides are diacetyl peroxide, dipropyl peroxide, dibutyl peroxide, dicapryl peroxide, dilauryl peroxide, BPO, dibenzoyl peroxide, p,p'-dichloro benzoyl peroxide, p,p'-dimethoxy benzoyl peroxide, p,p'-dimethyl benzoyl peroxide, and p,p'-dinitro dibenzoyl peroxide.

In a preferred embodiment of the infiltrant, the low viscous resin comprises 22% bis-GMA, 2,2-bis[4-(2-hydroxy-3-methacryloxypropoxy)phenyl]propane; 67% TEGDMA, triethylene glycol dimethacrylate; 10% ethanol; >1% DABE, ethyl 4-(dimethylamino)benzoate, and >1% camphorquinone.

The object of the present invention is further solved by a use of an infiltrant of the present invention for the manufacture of a medical product used in the prevention and/or treatment of a carious lesion in a subject in need thereof.

The object of the present invention is also solved by a use of hydrochloric acid for the manufacture of a medical product for the prevention and/or treatment of a carious lesion in a subject in need thereof, wherein the medical product is based on a gel comprising about 1-30% (w/w) of hydrochloric acid, preferably about 5-15% (w/w) of hydrochloric acid.

The object of the present invention is solved by a kit for infiltrating enamel, comprising:
(a) a conditioner comprising hydrochloric acid; and
(b) an infiltrant.

In one embodiment, the kit further comprises:
(c) a higher viscous light curing mixture of monomers.

In one embodiment of the kit, the conditioner (a) is based on a gel comprising about 1-30% (w/w) of hydrochloric acid, preferably about 5-15% (w/w) of hydrochloric acid.

In one embodiment of the kit, the infiltrant (b) is one according to the present invention.

In one embodiment, the kit further comprises at least one application strip and/or at least one cleaning strip and/or a separating means.

The object of the present invention is also solved by a kit for infiltrating enamel, comprising:
(a) an application strip comprising a conditioner comprising hydrochloric acid;
(b) an application strip comprising an infiltrant; and
(c) at least one cleaning strip.

In one embodiment, the kit additionally comprises:
(d) an application strip comprising a higher viscous light curing mixture of monomers.

In one embodiment, the kit additionally comprises:
(e) a separating means.

In one embodiment of the kit, the conditioner (a) is based on a gel comprising about 1-30% (w/w) of hydrochloric acid, preferably about 5-15% (w/w) of hydrochloric acid.

In one embodiment of the kit, the infiltrant (b) is one according to the present invention.

The object of the present invention is further solved by a method of infiltrating enamel, comprising the following steps:
(a) exposing an enamel area to be infiltrated to a conditioner comprising hydrochloric acid;
(b) exposing the enamel area conditioned in step (a) to an infiltrant; and
(c) curing the infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In a further embodiment, the conditioner further comprises additives selected from the group comprising glycerol, highly dispersed silicon dioxide and methylene blue.

In one embodiment, the infiltrant comprises at least one low viscous resin.

In a preferred embodiment, the low viscous resin is selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a particularly preferred embodiment, the low viscous resin is selected from the group comprising polymethacrylic acid and derivatives thereof.

In a most preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2,4,4-trimethylhexan; TEGDMA, triethylene glycol dimethacrylate; and HEMA, 2-hydroxyethyl methacrylate.

In a further embodiment, the infiltrant further comprises additives selected from the group comprising CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

The object of the present invention is further solved by a use of a method of infiltrating enamel according to the present invention for the prevention and/or treatment of a carious lesion in a subject in need thereof.

In one embodiment, the subject is a mammal, preferably a human.

The object of the present invention is also solved by a kit for infiltrating enamel, comprising at least the following:
(a) a conditioner comprising hydrochloric acid; and
(b) an infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In a further embodiment, the conditioner further comprises additives selected from the group comprising glycerol, highly dispersed silicon dioxide and methylene blue.

In one embodiment, the infiltrant comprises at least one low viscous resin.

In a preferred embodiment, the low viscous resin is selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate;

BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a particularly preferred embodiment, the low viscous resin is selected from the group comprising polymethacrylic acid and derivatives thereof.

In a most preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2,4,4-trim-ethylhexan; TEGDMA, triethylene glycol dimethacrylate; and HEMA, 2-hydroxyethyl methacrylate.

In a further embodiment, the infiltrant further comprises additives selected from the group comprising CQ, campho-roquinone; BL, benzil; DMBZ, dimethoxybenzoin; CEMA, N-(2-cyanoethyl)N-methylanilin; DMABEE, 4-N,N-diethy-laminobenzoic acid ethyl ester; DMABBEE, 4-N,N-diethy-laminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hy-droxy-4-methoxy benzophenone; TINP, 2(2'-hydroxy-5'-me-thylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Meth-ylenebis(6-t-butyl-4-ethylphenol); BPE, benzoic acid pheny-lester; MMMA, methyl methacrylate methanol adduct; CA, camphoric anhydride; HC ½, 2(3)-endo-hydroxyepicam-phor; TPP, triphenyl phosphane; TPSb, triphenyl stibane; DMDDA, dimethyl dodecylamine; DMTDA, dimethyl tet-radecylamine; DCHP, dicyclohexyl phthalate; DEHP, bis-(2-ethylhexyl) phthalate; and formaldehyde.

The object of the present invention is also solved by a use of a kit for infiltrating enamel for the prevention and/or treatment of a caries lesion in a subject in need thereof.

In one embodiment, the subject is a mammal, preferably a human.

The object of the present invention is also solved by a method for preparing the kit.

The object of the present invention is also solved by the use of hydrochloric acid for the manufacture of a medical product for the prevention and/or treatment of a carious lesion.

In one embodiment, the medical product is based on a gel comprising about 1-30% (w/w) of hydrochloric acid.

In a preferred embodiment, the medical product is based on a gel comprising about 5-15% (w/w) of hydrochloric acid.

In a further embodiment, the medical product further comprises additives selected from the group comprising glycerol, highly dispersed silicon dioxide and methylene blue.

The object of the present invention is also solved by a method for manufacturing the medical product.

The object of the present invention is also solved by an infiltrant comprising at least one low viscous resin.

In one embodiment, the low viscous resin is selected from the group comprising bis-GMA, 2,2-bis[4-(2-hydroxy-3-methacryloxypropoxy)phenyl]propane; bis-PMA, propoxy-lated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycar-bonylamino)-2,4,4-trimethylhexan; UPGMA, urethane bisphenol-A-dimethacrylate; TEGDMA, triethylene glycol dimethacrylate; TEGMMA, triethylene glycol monomethacrylate; TEEGDMA, tetraethylene glycol dimethacrylate; DEGDMA, diethylene glycol dimethacry-late; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a preferred embodiment, the low viscous resin is selected from the group comprising polymethacrylic acid and derivatives thereof.

In a particularly preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2, 4,4-trimethylhexan; TEGDMA, triethylene glycol dimethacrylate; and HEMA, 2-hydroxyethyl methacrylate.

In a further embodiment, the infiltrant further comprises additives selected from the group comprising CQ, campho-roquinone; BL, benzil; DMBZ, dimethoxybenzoin; CEMA, N-(2-cyanoethyl)N-methylanilin; DMABEE, 4-N N-diethy-laminobenzoic acid ethyl ester; DMABBEE, 4-N,N-diethy-laminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hy-droxy-4-methoxy benzophenone; TINP, 2(2'-hydroxy-5'-me-thylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Meth-ylenebis(6-t-butyl-4-ethylphenol); BPE, benzoic acid pheny-lester; MMMA, methyl methacrylate methanol adduct; CA, camphoric anhydride; HC ½, 2(3)-endo-hydroxyepicam-phor; TPP, triphenyl phosphane; TPSb, triphenyl stibane; DMDDA, dimethyl dodecylamine; DMTDA, dimethyl tet-radecylamine; DCHP, dicyclohexyl phthalate; DEHP, bis-(2-ethylhexyl) phthalate; and formaldehyde.

The object of the present invention is further solved by a method for preparing an infiltrant.

The object of the present invention is also solved by the use of an infiltrant, preferably an infiltrant according to the present invention, for the manufacture of a medical product for the prevention and/or treatment of a carious lesion.

The object of the present invention is also solved by a method for manufacturing the medical product.

The object of the present invention is further solved by a method for identifying an infiltrant having a penetration coefficient of >50 cm/s or an infiltrant comprising a low viscous light curing resin having a penetration coefficient of >50 cm/s using the following equation:

$$PC = \left(\frac{\gamma \cdot \cos\theta}{2\eta}\right) \qquad \text{-Equation 2-}$$

wherein:
PC refers to the penetration coefficient;
γ refers to the surface tension of the liquid resin (to air);
θ refers to the contact angle of the liquid resin (to enamel); and
η refers to the dynamic viscosity of the liquid resin.

The object of the present invention is further solved by an infiltrant identified using the method for identifying an infiltrant having a penetration coefficient of >50 cm/s or an infiltrant comprising a low viscous light curing resin having a penetration coefficient of >50 cm/s using the equation as given above (Equation 2).

The object of the present invention is further solved by an infiltrant having a penetration coefficient of >50 cm/s or comprising a low viscous light curing resin having a penetration coefficient of >50 cm/s.

In a preferred embodiment, the penetration coefficient of >50 cm/s is determined using Equation 2 above.

In a particularly preferred embodiment, the low viscous resin comprises 22% bis-GMA, 2,2-bis[4-(2-hydroxy-3-methacryloxypropoxy)phenyl]propane; 67% TEGDMA, triethylene glycol dimethacrylate; 10% ethanol; >1% DABE, ethyl 4-(dimethylamino)benzoate, and >1% camphorquinone.

The object of the present invention is further solved by a method for the prevention and/or treatment of a carious lesion using an infiltrant according to the present invention.

The object of the present invention is further solved by a use of an infiltrant according to the present invention for the manufacture of a medical product for the prevention and/or treatment of a carious lesion.

The object of the present invention is further solved by a method of infiltrating enamel for the prevention and/or treatment of a carious lesion in a subject in need thereof comprising the following steps:

(a) exposing an enamel area to be infiltrated to a conditioner comprising hydrochloric acid;
(b) exposing the enamel area conditioned in step (a) to an infiltrant having a penetration coefficient of >50 cm/s or to an infiltrant comprising a low viscous light curing resin having penetration coefficient of >50 cm/s; and
(c) curing the infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In one embodiment, the subject is a mammal, preferably a human.

The object of the present invention is further solved by a kit for infiltrating enamel, comprising:

(a) a conditioner comprising hydrochloric acid; and
(b) an infiltrant having a penetration coefficient of >50 cm/s or an infiltrant comprising a low viscous light curing resin having a penetration coefficient of >50 cm/s.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In one embodiment, the kit further comprises a device for application of the hydrochloric acid and/or the infiltrant.

The term "exposing" as used herein refers to any procedure by which the enamel is provided with the conditioner or the infiltrant. Mostly, an exposure will be achieved by simple application, e.g., by spreading. For that purpose, the kit may additionally comprise one or more devices suitable for supporting the application, e.g., a brush, a sponge, a tissue, a pipette, a syringe or such.

It is considered by the present invention that the conditioner may be removed prior to application of the infiltrant. Thus, the kit may additionally comprise any device for that purpose.

It is further considered by the present invention that surplus infiltrant may be removed. Thus, the kit may additionally comprise any device for that purpose.

Preferably, the conditioner is allowed to remain applied for about 60-300 seconds, more preferably, the conditioner is allowed to remain applied for about 90-120 seconds.

Preferably, the infiltrant is allowed to remain applied for up to about 120 seconds, more preferably, the infiltrant is allowed to remain applied for about 120 seconds.

Most preferably, the infiltrant has a penetration coefficient of >50 cm/s and is remained applied for less than 60 seconds.

Preferably, the infiltrant is applied twice.

An "enamel area to be infiltrated" preferably is an area comprising a carious lesion. However, in order to prevent such lesions, i.e. for prophylaxis, any carious damage may be also absent in this area.

The conditioner may alternatively be based on an aqueous solution or may also be embedded in a plaster.

It is also considered by the present invention that the conditioner may additionally comprise phosphoric acid up to about 40% (w/w), preferably in the range of about 20% to 37% (w/w).

"Curing of the infiltrant" is preferably achieved by light-induced polymerization.

To enable access to the approximal surface, a separation of the carious teeth could be performed using orthodontic elastics. This technique is well documented for diagnostic purposes.

The resins according to the present invention are further considered for use as dental adhesives and/or fissure sealants.

Said resins cited above may be used, e.g., within the infiltrant of the present invention, either separately or in any combination thereof.

The term "penetration coefficient" of an infiltrant refers to the ability of a liquid (infiltrant) to rapidly penetrate into a porous solid (caries lesion). It is composed of the following physical properties: surface tension to air ($\gamma$), contact angle to the solid ($\theta$) and dynamic viscosity ($\eta$) (see Equation 2).

The "surface tension $\gamma$" of an infiltrant (to air) refers to the force acting on a liquid-gas interface resulting in thin film on the surface. It is caused by an increased attraction of molecules at the surface of a liquid resulting from forces of attraction on fewer sides of the molecules.

The term "contact angle $\theta$" of an infiltrant (to enamel) refers to the tangent angle at the interface between the droplet of a liquid (infiltrant) and a solid surface (enamel).

The term "dynamic viscosity $\eta$" of an infiltrant refers to a measure of the resistance to flow of a fluid under an applied force. Dynamic viscosity is the tangential force per unit area (shear or tangential stress) required to move one horizontal plane with respect to the other at unit velocity when maintained a unit distance apart by the fluid (velocity gradient or rate of shear).

In conclusion, the present invention provides for an improved penetration of enamel lesions, e.g., initial or advanced enamel lesions, by an infiltrant. Within the prior art, methods of sealing enamel are available which, however, bear the risk of only superficially sealing the "pseudo-intact surface layer" but leaving the body of lesion insufficiently penetrated by the resin. Using the methods and means, e.g., the conditioner and/or the infiltrants or the low viscous resins, according to the present invention, occlusion of the body of lesion becomes possible.

First, by exposing an enamel area to be infiltrated to the conditioner comprising hydrochloric acid, the "pseudo-intact surface layer" is removed such that infiltration of carious areas by the infiltrant is greatly facilitated. Second, the resins cited above exhibit very low viscosity properties, and thus the infiltrant readily reaches the pores of the lesion to occlude them.

Furthermore, the present invention provides a method for determining the penetration coefficient (PC) of an infiltrant, allowing the identification and thus a preparation of an infiltrant having good penetrating properties while simultaneously exhibiting acceptable application times. On the basis of PCs determined according to said method, improved infiltrants, e.g., composites, can be developed.

By using the methods and means according to the present invention, invasive treatment of an enamel lesion may be prevented or at least delayed. Due to the non-operative character of the sealing procedure, the patient's compliance will be greatly enhanced. The method is well practicable with low costs. Finally, the inventive method may represent a therapeutic link between pure prophylaxis and invasive treatment of caries.

DETAILED DESCRIPTION OF THE INVENTION

Figure 3A:
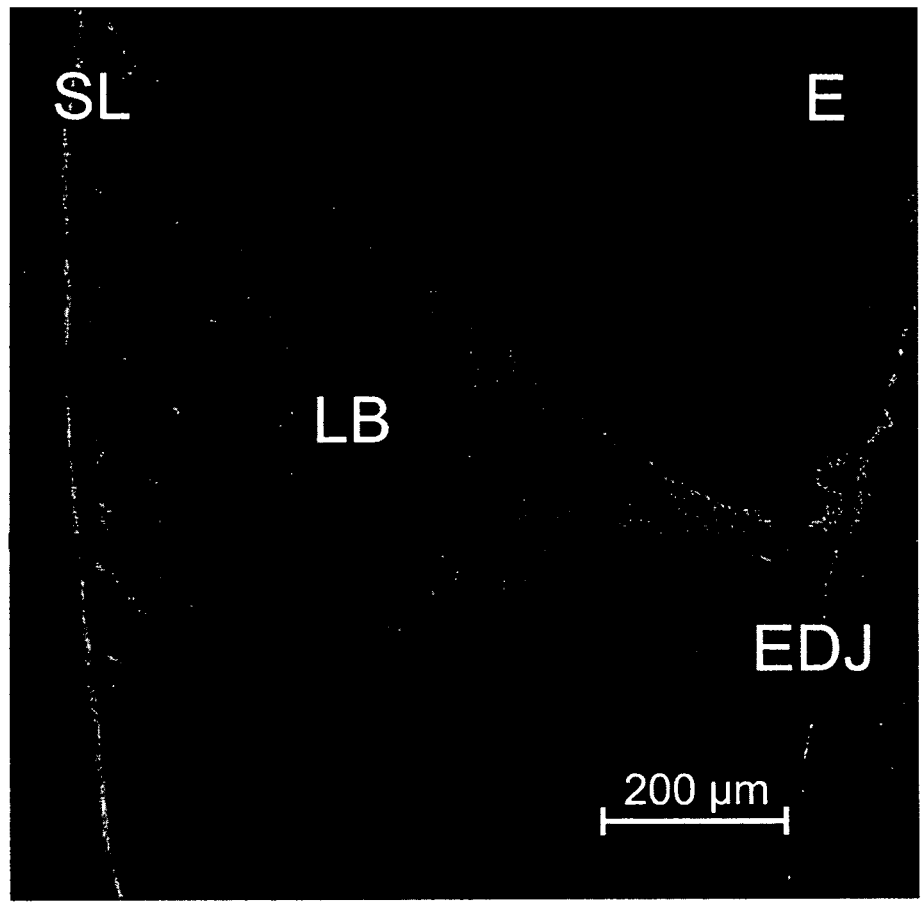
Figure 3B:
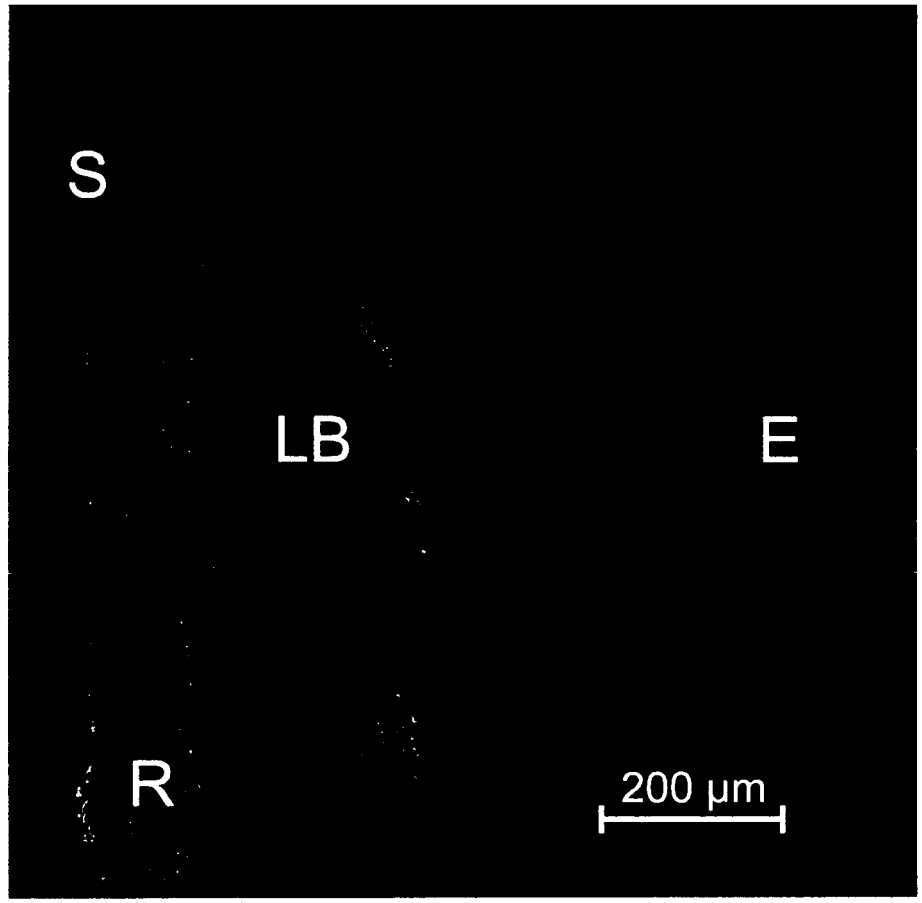
Figure 3C:
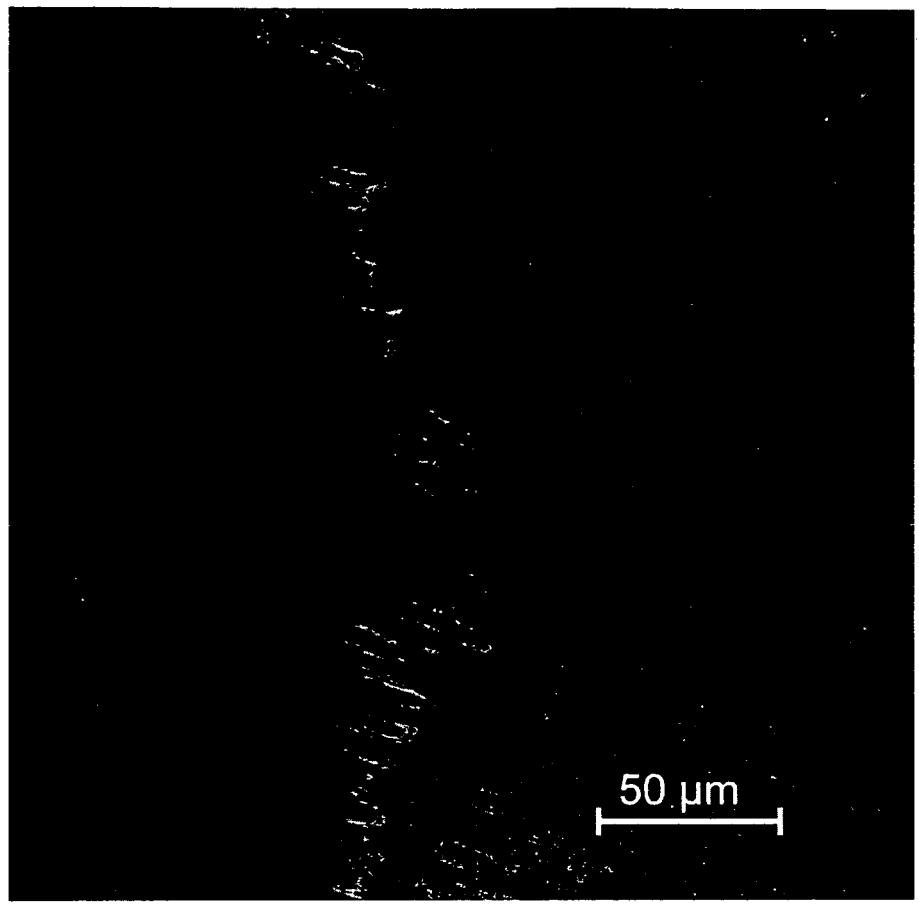

FIGS. 3A-3C show representative confocal microscopic images of resin infiltrated lesions (E: sound enamel; SL: surface layer; LB: lesion body; R: penetrated resin; EDJ: enamel-dentin junction; S: lesion surface); A: The surface layer of this $H_3PO_4$-etched caries lesion was not eroded completely. Therefore, only superficial resin penetration occurred (indicated by a fine rim of red fluorescence at the tooth surface); B: Deep resin penetration is observed in this HCl-etched lesion without visible surface layer remnants; C: Magnified image of an HCl-etched lesion (40×objective). The outermost 50-100 μm of prism cores are filled with resin. In non-infiltrated parts of the lesion body the highly porous prism centers show green fluorescence.

Figure 4:
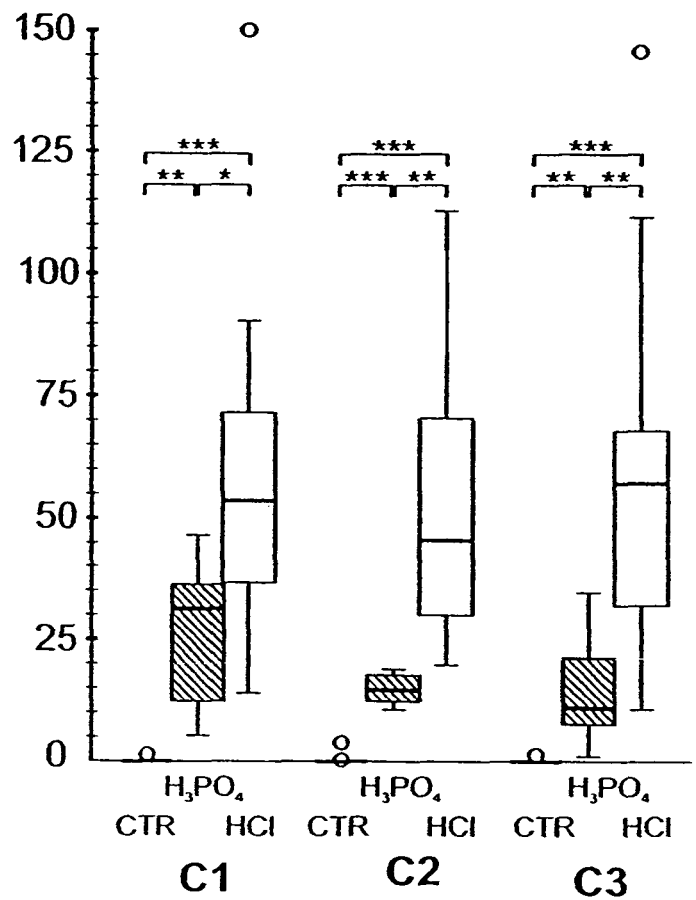

FIG. 4 shows mean penetration depths (y-axis) for various lesion extensions (box and whisker plots with quartiles and medians). Statistically significant differences between groups are indicated with asterisks (*p<0.05; p<0.01; *p<0.01; Wilcoxon/Mann-Whitney).

Figure 5A:
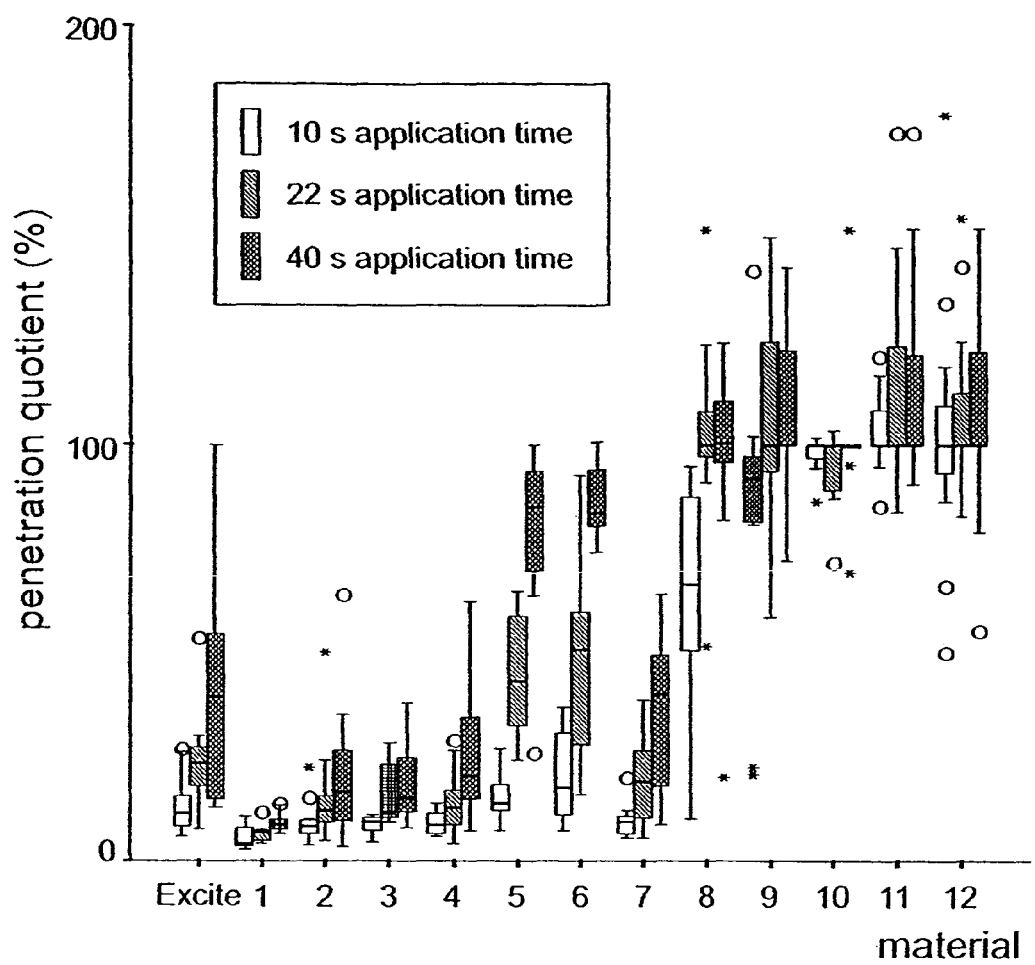
Figure 5B:
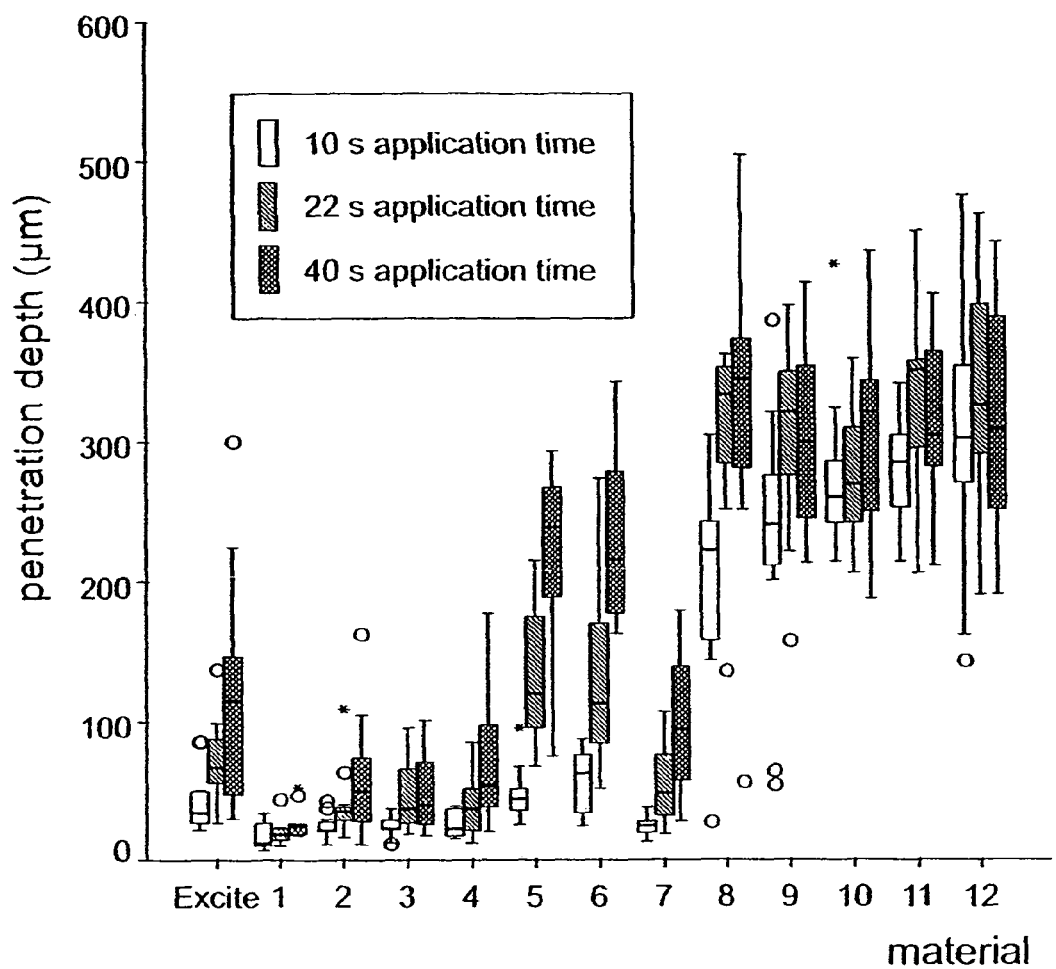

FIGS. 5A and 5B show penetration quotients (A) and absolute penetration depths (B) of the various materials (box-and-whisker plots with quartiles and medians).

Figure 6:
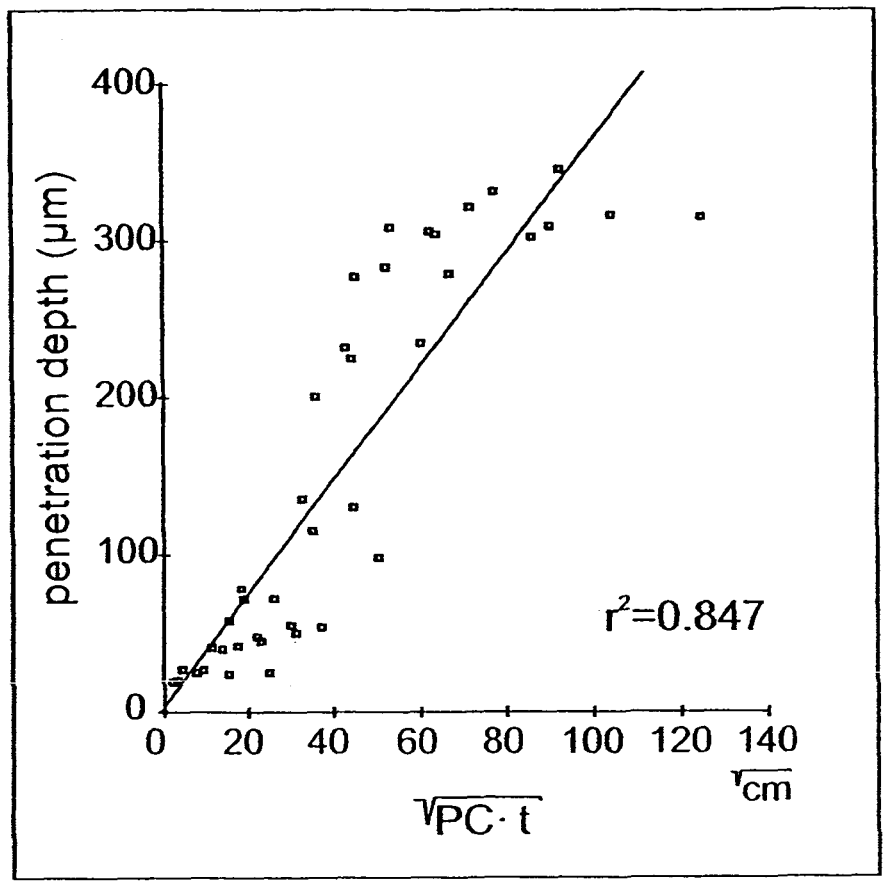

FIG. 6 shows a scatter plot of the square root of the product of penetration coefficient (PC) and time versus penetration depth.

Figure 7:
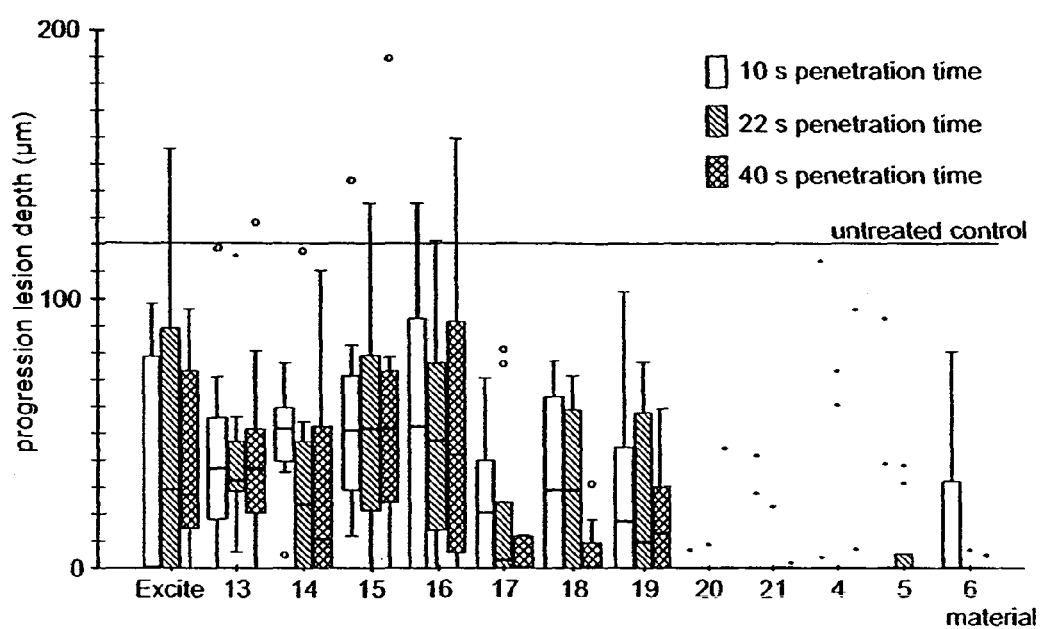

FIG. 7 shows percentage progressions of lesion depths for lesions treated with the different materials (box-and-whisker plots with quartiles and medians).

Figure 8:
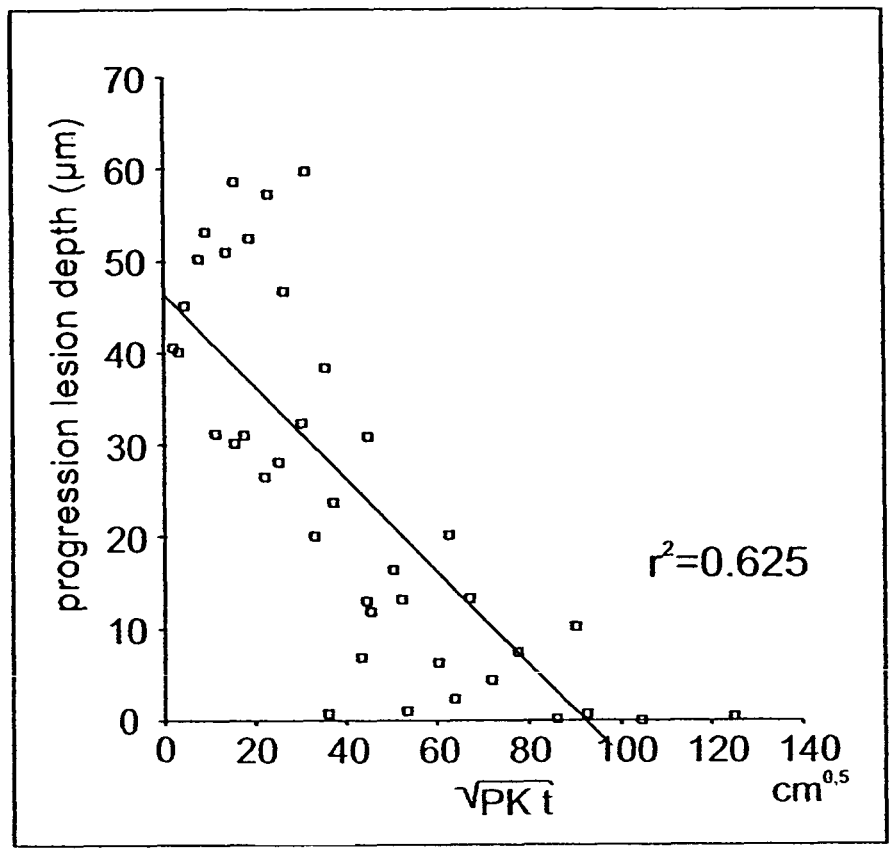

FIG. 8 shows a scatter plot of the square root of the product of penetration coefficient (PC) and time versus progression of lesion depth.

Figure 9:
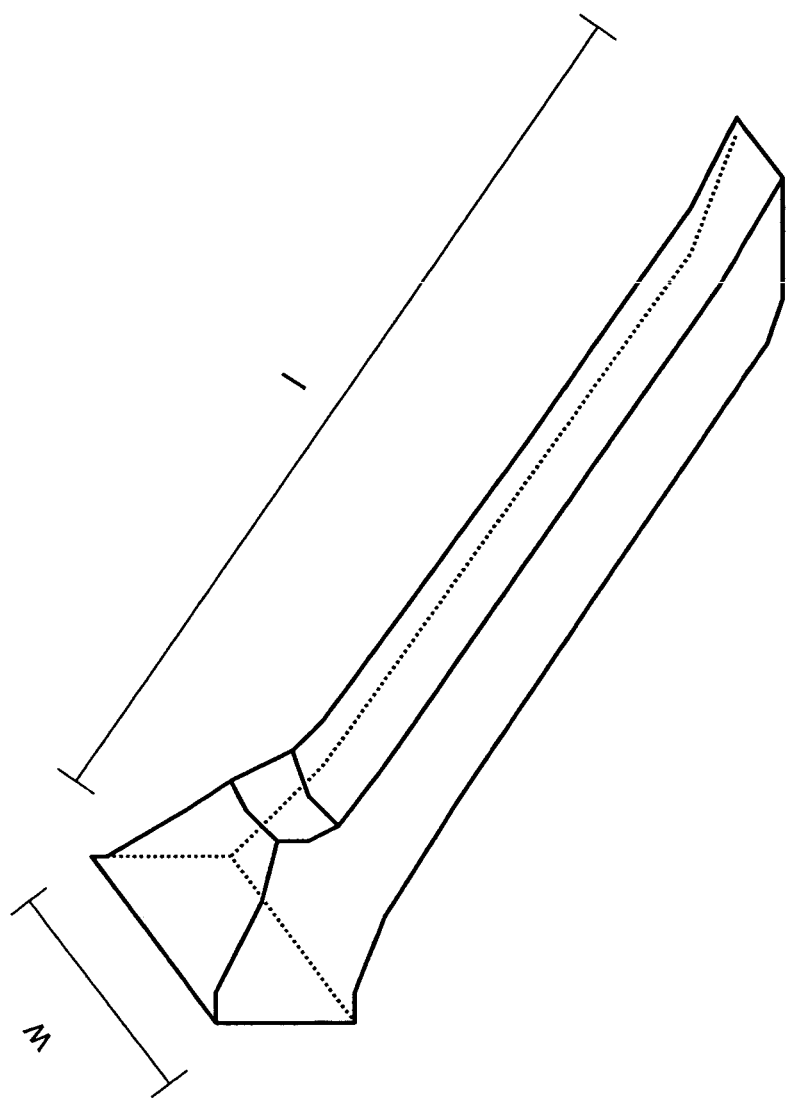

FIG. 9 shows a schematic plan view of a separating means of the present invention (w=width, e.g. up to approximately 2.5 mm; 1=length, e.g. approximately 12 mm).

Figures 10A, 10B:
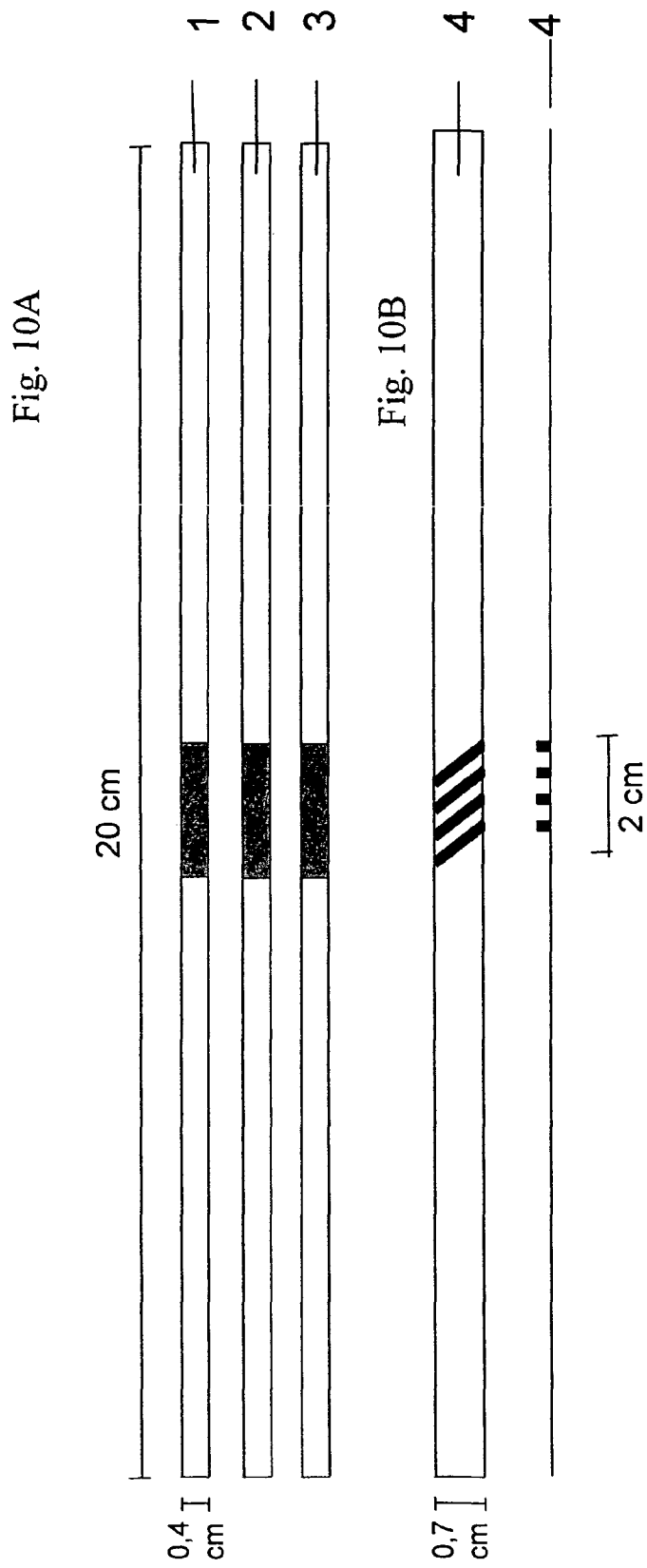

FIGS. 10A and B show schematic plan views of application strips (A) of the present invention, and schematic plan and side views of a cleaning strip (B) of the present invention. A: Application strips 1 to 3 comprising delivery pads adapted to applying hydrochlorid acid, infiltrant and a higher viscous light curing mixture of monomers, respectively. B: Cleaning strip 4 comprising flexible cleaning laps.

EXAMPLES

Example 1

Effect of the Pre-Treatment with a Conditioner Comprising Hydrochloric Acid

1. Material and Methods 1.1 Sample Preparation

Extracted human molars and premolars, showing approximal white spots were cut across the demineralizations. One-hundred-twenty lesions confined to the outer enamel were selected. The cut surface as well as half of each lesion, thus serving as control, was covered with nail varnish. Subsequently, the lesions were etched with either phosphoric (37%) or hydrochloric (5% or 15%) acid gel for 30 to 120 seconds (n=10).

1.2 Visualization

The specimens were dried for 5 minutes in a silicone hose, closed at one end with a stopper, and separated with silicone rings. Subsequently, Spurr's resin (Spurr A R. A low-viscosity epoxy resin embedding medium for electron microscopy. *J Ultrastruct Res,* 1969, 26:31-43), labeled with 0.1 mmol/l of the fluorescent dye Rhodamine B Isothiocyanate (RITC), was doused over the specimens and the hose was closed with another stopper. The resin was cured in an autoclave (Ivomat IP3; Ivoclar Vivadent, Schaan, Liechtenstein) at 0.8 MPa and 70° C. for 8 hours. Under this pressure, the very low viscous resin penetrated into the remaining pores of the lesion. After curing, the specimens were cut, fixed on object holders, parallelized and polished up to 4000 grit (Exakt Mikroschleifsystem; Exakt Apparatebau). This infiltration technique was termed VIsualisation by Resin INfiltration (VIRIN).

1.3 CLSM Imaging

The specimens were studied using a Confocal Laser Scanning Microscope (CLSM) (Leica TCS NT; Leica, Heidelberg, Germany). The excitation light was generated with an Ar/Kr-Laser and had a maximum wavelength at 560 nm. The images were recorded in fluorescent mode. The emitted light was conducted through a 590 nm long pass filter to make sure that only fluorescent light was detected and reflected light was suppressed. Specimens were observed with a 40×objective using oil immersion. The observed layer was approximately 10 μm below the surface. Laser beam intensity and photo multiplier amplification were kept constant during the investigation. The images (250×250 μm) were taken with a resolution of 1024×1024 pixels and 256 pseudo color steps (red/black) and analyzed using the ImageJ Program (NIH; Rockville Pike, Md., USA).

2. Results

The thickness of the surface layers in the control and the etched parts as well as the erosions in the sound and diseased tissues were measured. Etching with $H_3PO_4$ gel for 30 seconds did not alter the thickness of the surface layer significantly (p>0.05; t-test). However, the surface layer reduction was significantly increased in lesions etched with 15% HCl gel for 90 seconds compared to those etched with $H_3PO_4$ gel for 30 or 90 seconds (p<0.05; ANOVA). No significant differences in the depths of erosion in the lesions compared to sound enamel could be observed (p>0.05; t-test).

Figure 1:
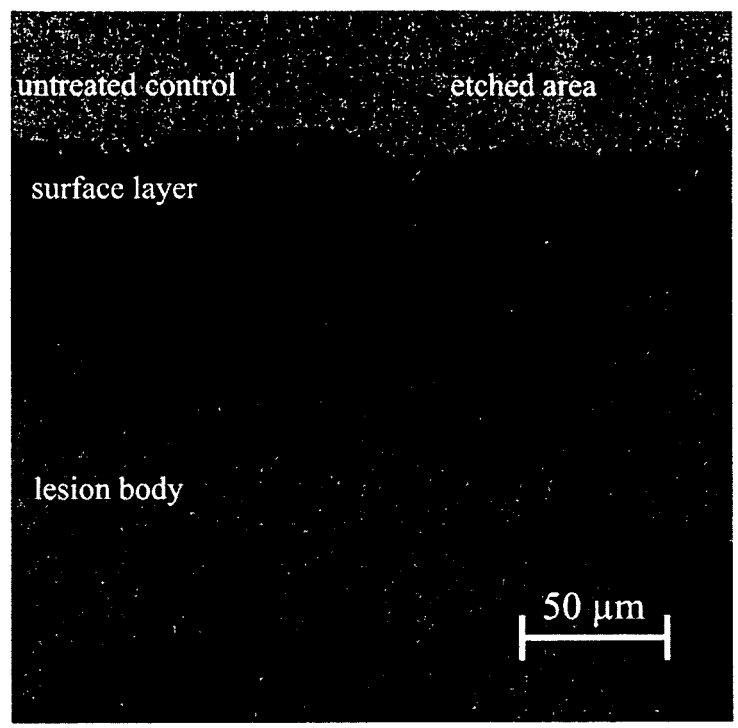
FIG. 1 shows an initial enamel carious lesion after conditioning with 37% of phosphoric acid gel for 30 seconds (results obtained by the Confocal Laser Scanning Microscope, CLSM, imaging technique).
Figure 2:
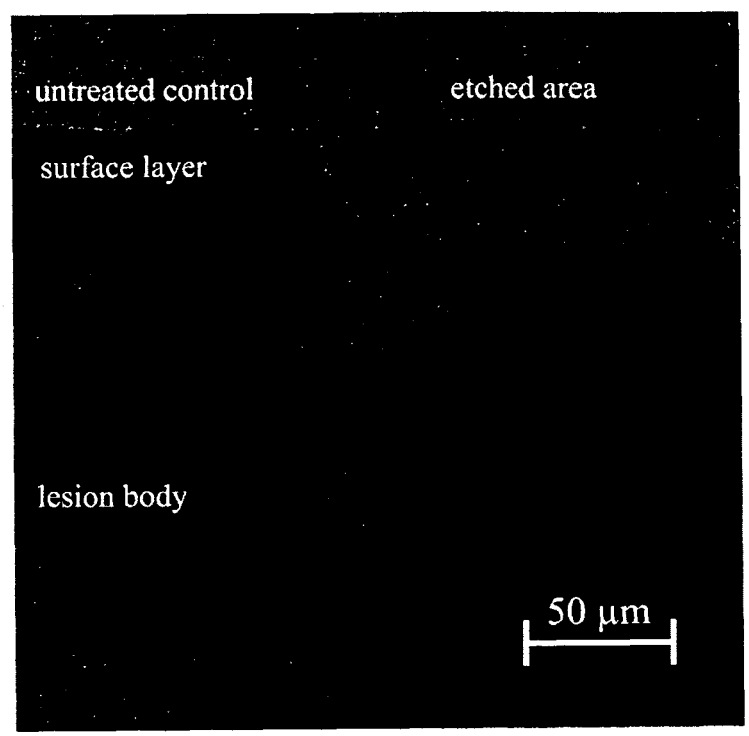
FIG. 2 shows an initial enamel carious lesion after conditioning with 15% hydrochloric acid gel for 120 seconds (results obtained by CLSM).

In FIG. 1, it is shown that pre-treatment of initial enamel carious lesions with 37% of phosphoric acid gel for 30 seconds resulted in only insufficient etching of the "pseudo-intact surface layer". Thus, this kind of pre-treatment is not capable of destabilizing the surface layer to an extent necessary for optimal penetration of the infiltrant. In consequence, sealing will be only superficial. Incomplete infiltration, however, does not protect from organic acids and dissolution of enamel and erosion will further proceed. In FIG. 2, it is shown that pre-treatment with 15% of hydrochloric acid gel for 120 seconds resulted in complete removal of the "pseudo-intact surface layer".

It can be concluded that a reliable reduction of the surface layer can be achieved by etching with 15% hydrochloric acid gel for 90 to 120 seconds.

Example 2

Resin Infiltration of Natural Caries Lesions after Etching with Phosphoric and Hydrochloric Acid Gels in vitro 1. Material and Methods Extracted human molars and premolars showing proximal white spot lesions were used in this study. After careful cleaning from soft tissues teeth were stored in 20% ethanol solution up to usage. Teeth were examined using a 20×stereo microscope (Stemi S V 11; Carl Zeiss, Oberkochen, Germany) and cavitated as well as damaged lesions were excluded.

For radiographic examination teeth were positioned in a silicone base with the buccal aspect facing to the radiographic tube (Heliodent M D; Siemens, Bensheim, Germany). To simulate cheek scatter a 15 mm wall of clear Perspex was placed between the tube and the teeth. Standardized radiographs (0.12 seconds, 60 kV, 7.5 mA) were taken from each tooth (Ektaspeed; Kodak, Stuttgart, Germany) and developed using an automatic processor (XR 24-II; Dürr Dental, Bietigheim-Bissingen, Germany). The radiographic lesion depths were assessed by two examiners independently and scored (Marthaler T M and Germann M. Radiographic and visual appearance of small smooth surface caries lesions studied on extracted teeth. *Caries Res*, 1970, 224-242): no translucency (R0), translucency confined to the outer half on enamel (R1), translucency to the inner half of enamel (R2), translucency to the outer half of dentin (R3) and to the inner half of dentin (R4). In case of disagreement in assessment of radiographic lesion depth a consensus rank was concerted.

The roots of the teeth were removed and the crowns were cut across the carious lesions perpendicular to the surface (Band Saw; Exakt Apparatebau, Norderstedt, Germany) providing two halves of each lesion. Subsequently, the cut surfaces were examined (stereo microscope) and classified with respect to the histological lesion extension (C1-C3). Lesions extending into the inner half of dentin (C4) were excluded. Corresponding lesion halves showing equal caries extension were assigned to the treatment (TRT) group (n=10 each). When corresponding lesion halves differed in extension, only the deeper one was used as control (CTR; n=10).

Subsequently, the cut surfaces were covered with nail varnish. In the TRT groups corresponding lesion halves were either etched with 37% phosphoric acid gel ($H_3PO_4$; total etch; Ivoclar Vivadent, Schaan, Liechtenstein) or with an experimental 15% hydrochloric acid gel (HCl). The HCl gel contained hydrochloric acid 15%, glycerol 19%, highly dispersed silicon dioxide 8% and methylene blue 0.01% in aqueous solution. After 120 seconds the gels were rinsed thoroughly with water spray for 30 seconds. In the CTR group no acid etching was performed. Lesions were immersed with pure ethanol for 30 seconds and subsequently dried for 60 seconds using oil free compressed air.

A dental adhesive (Excite; Ivoclar Vivadent) labeled with 0.1% tetramethylrhodamine isothiocyanate (TRITC; Sigma Aldrich, Steinheim, Germany) was applied onto the lesion surfaces. The resin was allowed to penetrate into the lesions for 5 minutes. Subsequently, excessive material was removed and the resin was light cured for 30 seconds (Translux C L; Heraeus Kulzer, Hanau, Germany) at 400 mW/cm$^2$. The nail varnish was carefully removed, and specimen halves were fixed on object holders parallel to the cut surface and polished (Exakt Mikroschleifsystem, Abrasive Paper 2400, 4000; Exakt Apparatebau, Norderstedt, Germany). In order to stain remaining pores, the specimens were immersed in 50% ethanol solution containing 100 µM/l sodium fluorescein (Sigma Aldrich) for 3 hours.

Specimens were observed using a confocal laser scanning microscope (CLSM Leica TCS NT; Leica, Heidelberg, Germany) in double fluorescence mode using a 10×objective. The excitation light had two wavelength maxima at 488 and 568 nm. The emitted light was split by a 580 nm reflection short pass filter and paned through a 525/50 nm band pass filter for FITC and a 590 nm long pass filter for RITC detection. Images with a lateral dimension of 1000×1000 µm$^2$ and a resolution of 1024×1024 pixels were recorded and analyzed using AxioVision LE software (Zeiss, Oberkochen, Germany). Penetration depths and thickness of the (residual) surface layer for the lesion halves were measured at up to 10 defined points (depending on the lesion size; indicated by a 100 µm grit) and mean values were calculated.

Statistical analysis was performed using SPSS software (SPSS for Windows 11.5.1; SPSS Inc., Chicago, Ill., USA). Data were checked for normal distribution using the Kolgomorov Smirnov test. To analyze differences between lesion halves/acid gels Wilcoxon test for paired samples was used. For comparison between unpaired groups Mann-Whitney tests and Kruskal-Wallis tests were performed.

2. Results

In the CLSM images, the penetrated resin showed a red fluorescence, whereas remaining pores within the lesion as well as dentin appeared green (FIG. 3A-C). Solid material as sound enamel or the surface layer was displayed black.

Penetration depths varied considerably. FIG. 4 shows the penetration depths of the various groups for different caries extensions. For lesion halves etched with HCl gel the mean penetration depth (standard deviation) [58 (37) µm] was significantly higher compared with those of lesions treated with $H_3PO_4$ gel [18 (11) µm] (p<0.001; Wilcoxon). Without acid etching no resin penetration was found [0 (1) µm]. Within treatment groups no significant difference for penetration depths could be observed between various lesion extensions (C1-C3) (p>0.05; Kruskal-Wallis). Similarly, penetration depths were comparable for radiographic lesion depths (R1-R3) (p>0.05; Table 1).

For those lesions where the surface layer was completely removed (CTR n=0; $H_3PO_4$ n=2; HCl n=8) significantly higher (p<0.01; Mann-Whitney) mean penetration depths [65 (35) µm] could be found compared to lesions, where residues of the surface layer remained after etching [33 (31) µm]. Surface layer thickness was significantly reduced after HCl etching [20 (18) µm] compared to lesions etched with phosphoric acid [37 (25) µm] and to the non-etched CTR group [42 (23) µm] (p>0.05; Mann-Whitney).

TABLE 1

Mean penetration depths [μm (standard deviations)] for the various radiological caries extensions.

| group | | R0 | R1 | R2 | R3 |
|---|---|---|---|---|---|
| | | | radiolucency | | |
| CTR | | $0\,(0)_{n=8}$ | $0\,(0)_{n=10}$ | $1\,(1)_{n=8}$ | $0\,(0)_{n=4}$ |
| TRT | $H_3PO_4$ | $25\,(15)_{n=6}$ | $17\,(12)_{n=10}$ | $16\,(7)_{n=8}$ | $16\,(10)_{n=6}$ |
| | HCl | $47\,(27)_{n=6}$ | $65\,(41)_{n=10}$ | $52\,(27)_{n=8}$ | $67\,(52)_{n=6}$ |

Example 3

Evaluation of the PCs of Experimental Infiltrants

The aim of this investigation was the evaluation of the PCs of 66 experimental composite resins intended to infiltrate enamel lesions (infiltrants).

1. Material and Methods

A total of 66 experimental infiltrants containing two of the monomers BisGMA, UDMA, TEGDMA and HEMA in variable weight proportions each (100:0; 75:25; 50:50; 25:75; 0:100) as well as ethanol (0%, 10% or 20%) were prepared (Table 2). For each experimental resin, 10 g were mixed up in brown glass jars according to Table 2. To avoid premature polymerization, the resins were stored at 4° C. until use. To determine PCs of the experimental infiltrants, contact angles, surface tensions, and viscosities were measured.

TABLE 2

Composition (weight percent) and measured results of experimental infiltrants. Means and standard deviations (SD) are given for contact angles, surface tensions, dynamic viscosities and resulting penetration coefficients (PCs). In addition, the consistency after light curing is displayed.

| N° | BisGMA (%) | TEGDMA (%) | HEMA (%) | UDMA (%) | EtOH (%) | Contact Angle θ (°) | (cos) | Viscosity η (mPa s) | Surface Tension γ (mN/m) | PC (cm/s) | Consistency after curing |
|---|---|---|---|---|---|---|---|---|---|---|---|
| 1 | 100 | | | | | * | * | * | * | * | hard |
| 2 | 90 | | | | 10 | 54.2 (2.5) | 0.58 | 6637.0 (1.2) | 40.6 (0.1) | 0.2 | hard |
| 3 | 80 | | | | 20 | 47.8 (0.9) | 0.67 | 750.3 (2.3) | 34.7 (0.1) | 1.6 | hard |
| 4 | | 100 | | | | 7.0 (0.4) | 0.99 | 8.4 (0.0) | 34.7 (0.0) | 204.1 | hard |
| 5 | | 90 | | | 10 | 3.7 (0.1) | 1.00 | 5.8 (0.0) | 31.5 (0.0) | 273.1 | hard |
| 6 | | 80 | | | 20 | 3.2 (0.1) | 1.00 | 3.6 (0.0) | 28.0 (0.0) | 390.7 | hard |
| 7 | | | 100 | | | 11.0 (0.6) | 0.98 | 5.2 (0.0) | 34.6 (0.0) | 326.8 | hard |
| 8 | | | 90 | | 10 | 7.5 (0.5) | 0.99 | 4.0 (0.0) | 32.1 (0.0) | 393.8 | viscous |
| 9 | | | 80 | | 20 | 4.2 (0.4) | 1.00 | 3.2 (0.0) | 30.2 (0.0) | 474.9 | liquid |
| 10 | | | | 100 | | 44.9 (3.2) | 0.71 | * | * | * | hard |
| 11 | | | | 90 | 10 | 33.6 (0.6) | 0.83 | 412.0 (9.7) | 35.4 (0.0) | 3.6 | hard |
| 12 | | | | 80 | 20 | 32.5 (1.0) | 0.84 | 84.5 (0.0) | 33.3 (0.0) | 16.6 | hard |
| 13 | 75 | 25 | | | | 30.5 (1.2) | 0.86 | 3345.7 (4.0) | 38.4 (0.0) | 0.5 | hard |
| 14 | 67.5 | 22.5 | | | 10 | 23.8 (0.8) | 0.91 | 272.2 (0.3) | 35.5 (0.0) | 6.0 | hard |
| 15 | 60 | 20 | | | 20 | 17.0 (0.5) | 0.96 | 59.0 (0.0) | 30.1 (0.1) | 24.4 | hard |
| 16 | 50 | 50 | | | | 26.1 (2.9) | 0.90 | 186.4 (0.1) | 36.5 (0.0) | 8.8 | hard |
| 17 | 45 | 45 | | | 10 | 20.8 (1.6) | 0.93 | 31.4 (0.0) | 33.2 (0.0) | 49.4 | hard |
| 18 | 40 | 40 | | | 20 | 10.1 (0.1) | 0.98 | 16.4 (0.0) | 30.3 (0.0) | 91.1 | hard |
| 19 | 25 | 75 | | | | 16.9 (0.9) | 0.96 | 26.9 (0.0) | 35.5 (0.0) | 63.3 | hard |
| 20 | 22.5 | 67.5 | | | 10 | 5.1 (0.7) | 1.00 | 12.7 (0.0) | 33.0 (0.0) | 129.3 | hard |
| 21 | 20 | 60 | | | 20 | 5.0 (0.9) | 1.00 | 7.8 (0.0) | 29.1 (0.0) | 185.4 | hard |
| 22 | 75 | | 25 | | | 33.2 (1.2) | 0.84 | 2344.1 (2.4) | 38.3 (0.0) | 0.7 | hard |
| 23 | 67.5 | | 22.5 | | 10 | 29.7 (1.1) | 0.87 | 243.5 (0.2) | 34.9 (0.0) | 6.2 | hard |
| 24 | 60 | | 20 | | 20 | 28.6 (2.2) | 0.88 | 60.8 (0.2) | 30.5 (0.0) | 22.1 | hard |
| 25 | 50 | | 50 | | | 14.4 (0.2) | 0.97 | 52.4 (0.2) | 36.3 (0.0) | 33.6 | hard |
| 26 | 45 | | 45 | | 10 | 12.4 (0.8) | 0.98 | 37.2 (0.0) | 33.3 (0.0) | 43.6 | hard |
| 27 | 40 | | 40 | | 20 | 5.5 (0.8) | 1.00 | 17.7 (0.0) | 30.8 (0.0) | 86.7 | hard |
| 28 | 25 | | 75 | | | 14.4 (1.9) | 0.97 | 18.5 (0.0) | 35.4 (0.0) | 92.7 | hard |
| 29 | 22.5 | | 67.5 | | 10 | 8.9 (1.0) | 1.00 | 10.9 (0.0) | 32.5 (0.0) | 149.3 | hard |
| 30 | 20 | | 60 | | 20 | 5.1 (0.3) | 1.00 | 7.0 (0.0) | 30.4 (0.0) | 216.5 | rubbery |
| 31 | 75 | | | 25 | | 53.9 (2.2) | 0.59 | * | * | * | hard |
| 32 | 67.5 | | | 22.5 | 10 | 49.1 (3.0) | 0.65 | 1919.8 (26.4) | 38.7 (0.0) | 0.7 | hard |
| 33 | 60 | | | 20 | 20 | 44.7 (0.7) | 0.71 | 238.1 (0.2) | 30.8 (0.0) | 4.6 | hard |
| 34 | 50 | | | 50 | | 52.2 (3.4) | 0.61 | * | * | * | hard |
| 35 | 45 | | | 45 | 10 | 41.3 (1.0) | 0.75 | 1350.4 (2.4) | 36.9 (0.1) | 1.0 | hard |
| 36 | 40 | | | 40 | 20 | 38.9 (0.2) | 0.78 | 156.3 (0.2) | 30.6 (0.0) | 7.6 | hard |
| 37 | 25 | | | 75 | | 48.0 (3.0) | 0.67 | * | * | * | hard |
| 38 | 22.5 | | | 67.5 | 10 | 39.1 (1.3) | 0.78 | 737.3 (0.7) | 35.8 (0.0) | 1.9 | hard |
| 39 | 20 | | | 60 | 20 | 35.6 (5.6) | 0.81 | 123.8 (0.1) | 30.8 (0.0) | 10.1 | hard |
| 40 | | 75 | 25 | | | 7.5 (0.1) | 0.99 | 7.2 (0.0) | 34.5 (0.0) | 237.9 | hard |
| 41 | | 67.5 | 22.5 | | 10 | 4.8 (1.0) | 1.00 | 4.9 (0.0) | 32.3 (0.0) | 332.1 | hard |
| 42 | | 60 | 20 | | 20 | 3.6 (0.9) | 1.00 | 3.4 (0.0) | 30.0 (0.0) | 433.0 | hard |
| 43 | | 50 | 50 | | | 8.3 (0.5) | 0.99 | 6.6 (0.0) | 34.6 (0.0) | 259.6 | hard |
| 44 | | 45 | 45 | | 10 | 4.9 (0.6) | 1.00 | 4.4 (0.0) | 32.0 (0.0) | 363.8 | hard |
| 45 | | 40 | 40 | | 20 | 4.1 (0.9) | 1.00 | 3.5 (0.0) | 30.0 (0.0) | 429.9 | rubbery |
| 46 | | 25 | 75 | | | 9.1 (0.9) | 0.99 | 6.1 (0.0) | 34.6 (0.0) | 277.6 | hard |
| 47 | | 22.5 | 67.5 | | 10 | 7.1 (0.7) | 0.99 | 4.2 (0.0) | 32.2 (0.0) | 382.4 | hard |
| 48 | | 20 | 60 | | 20 | 4.1 (0.2) | 1.00 | 3.3 (0.0) | 30.0 (0.0) | 456.5 | pliant |
| 49 | | 25 | | 75 | | 33.3 (1.2) | 0.84 | 603.3 (2.0) | 34.9 (0.0) | 2.4 | hard |

TABLE 2-continued

Composition (weight percent) and measured results of experimental infiltrants.
Means and standard deviations (SD) are given for contact angles, surface tensions,
dynamic viscosities and resulting penetration coefficients (PCs). In addition, the
consistency after light curing is displayed.

| N° | BisGMA (%) | TEGDMA (%) | HEMA (%) | UDMA (%) | EtOH (%) | Contact Angle θ (°) | (cos) | Viscosity η (mPa s) | Surface Tension γ (mN/m) | PC (cm/s) | Consistency after curing |
|----|------|------|------|------|-----|------------|------|------------|------------|-------|---------|
| 50 | 22.5 |      |      | 67.5 | 10  | 28.5 (1.1) | 0.88 | 83.4 (0.4) | 33.6 (0.0) | 17.7  | hard |
| 51 | 20   |      |      | 60   | 20  | 19.8 (0.7) | 0.94 | 29.5 (0.1) | 29.8 (0.1) | 47.5  | hard |
| 52 | 50   |      |      | 50   |     | 27.0 (1.6) | 0.89 | 80.9 (5.9) | 35.2 (0.3) | 19.4  | hard |
| 53 | 45   |      |      | 45   | 10  | 11.4 (0.7) | 0.98 | 25.5 (0.1) | 32.3 (0.0) | 62.0  | hard |
| 54 | 40   |      |      | 40   | 20  | 6.1 (0.5)  | 0.99 | 13.0 (0.0) | 29.4 (0.0) | 112.5 | hard |
| 55 | 75   |      |      | 25   |     | 9.2 (9.2)  | 0.99 | 21.4 (0.0) | 35.2 (0.0) | 81.0  | hard |
| 56 | 67.5 |      |      | 22.5 | 10  | 7.8 (0.5)  | 1.00 | 9.3 (0.1)  | 31.8 (0.0) | 171.0 | hard |
| 57 | 60   |      |      | 20   | 20  | 5.9 (1.2)  | 0.99 | 6.9 (0.0)  | 29.2 (0.0) | 211.6 | hard |
| 58 |      | 25   | 75   |      |     | 32.3 (1.5) | 0.84 | 357.4 (0.2)| 36.5 (0.0) | 4.3   | hard |
| 59 |      | 22.5 | 67.5 |      | 10  | 11.7 (0.4) | 0.98 | 71.7 (0.1) | 33.2 (0.0) | 22.7  | hard |
| 60 |      | 20   | 60   |      | 20  | 9.0 (1.4)  | 0.99 | 33.6 (0.0) | 30.6 (0.0) | 45.0  | hard |
| 61 |      | 50   | 50   |      |     | 12.1 (1.2) | 0.98 | 52.5 (0.0) | 36.0 (0.0) | 33.5  | hard |
| 62 |      | 45   | 45   |      | 10  | 10.3 (1.5) | 0.98 | 20.3 (0.0) | 32.6 (0.0) | 79.1  | Hard |
| 63 |      | 40   | 40   |      | 20  | 4.3 (0.3)  | 1.00 | 10.8 (0.0) | 30.2 (0.0) | 139.9 | Rubbery |
| 64 |      | 75   | 25   |      |     | 11.3 (1.2) | 0.98 | 12.9 (0.0) | 35.2 (0.1) | 134.3 | Hard |
| 65 |      | 67.5 | 22.5 |      | 10  | 8.1 (1.0)  | 0.99 | 9.1 (0.0)  | 32.5 (0.0) | 177.9 | Hard |
| 66 |      | 60   | 20   |      | 20  | 4.4 (0.1)  | 1.00 | 6.3 (0.0)  | 30.4 (0.0) | 239.5 | Rubbery |

Contact angle measurements were performed to polished bovine enamel. From the labial surfaces of bovine incisors, enamel disks (approximately 5×5×3 mm$^3$) were prepared (Band Saw Extract 300 cl; Extrakt Apparatebau, Norderstedt, Germany), embedded in methacrylate resin (Technovit 4071; Heraeus Kulzer, Hanau, Germany), and their surfaces were ground flat and polished (Polishing Machine Phoenix Alpha; Buehler, Düsseldorf, Germany; Abrasive Paper 600, 1200, 2400, 4000; Exact Apparatebau). Until usage, the specimens were stored in distilled water. Prior to each measurement, the surfaces were dried and cleaned using 100% ethanol.

To measure the contact angles of the resins, a camera based goniometer was used (G10; Krüss, Hamburg, Germany). Droplets of the liquid resins (approximately 1 µl) were placed on the enamel surface by means of a micro syringe. After 10 seconds, an image was recorded and analyzed using drop shape analysis software (DSA 10; Krüss). For each resin, the mean contact angel of three measurements was calculated. To avoid surface contamination, each measurement was performed on a new enamel disk.

Surface tensions were measured using a ring processor tensiometer (K12; Krüss). To achieve air saturation, a cup containing ethanol was placed into the metering chamber when solvent containing mixtures were gauged. Five ml of each composite were given into a Teflon mould, and the testing ring (platinum iridium alloy, RI 12; Krüss) was positioned close to the liquid surface. Measurements were performed automatically. Depending on the variance of the measured values, the device stopped gauging automatically after 5 to 20 cycles.

Kinematical viscosities were determined using a mirco-Ubbelohde processor viscosimeter (Schott; Mainz, Germany) at 25° C. For low viscous resins, glass capillaries with a capillary constant of 0.1 mm$^2 \cdot$s$^{-2}$ were used. High viscous composites were tested using capillaries with a capillary constant of 10 mm$^2 \cdot$s$^{-2}$. Three measurements were performed automatically and means and standard deviations (SD) were assessed for each material. Dynamic viscosities were calculated by multiplying the measured values with the densities of the resins. Densities of the experimental composites were calculated from data provided by the manufacturer of the monomers.

To evaluate the hardening capacities of the experimental infiltrants, 0.5% DABE and 0.5% Camphorquinone were added. The resins were applied to standardized moulds (7×4×2 mm$^3$), and light cured at 400 mW/cm$^2$ for 60 seconds (Translux C L; Hereaus Kulzer). Subsequently, their consistencies were assessed qualitatively and graded into the categories "hard", "pliant", "rubbery", "viscous", or "liquid".

2. Results

The results for the experimental infiltrants are shown in Table 1. The greatest differences between the resins were found for the viscosities (3.2-6637.0 mPa·s). Resin mixtures containing high amounts of HEMA and TEGDMA showed low viscosities and high PCs. In contrast, BisGMA and UDMA showed increased viscosities and decreased PCs. Five experimental resins containing high amounts of BisGMA or UDMA were too viscous to be measured with the available devices. Although high variations were found for the contact angles (3.2-54.2°), their impacts on PCs were limited as they only account to PC proportional to their cosine. The addition of ethanol decreased viscosities, surface tensions, and contact angles of all mixtures leading to increased penetration coefficients for all monomer combinations. The highest PCs were found for composites containing TEGDMA, HEMA, and 20% ethanol. Composites containing high amounts of HEMA and ethanol did not cure sufficiently, leading to rubbery or liquid materials (Table 2).

Example 4

Influence of PC on Penetration Speed

The aim of this in vitro study was to compare the penetration quotients (PQ=penetration depth/lesion depth) of twelve experimental infiltrants showing different PCs with an adhesive (Excite®; Vivadent).

1. Materials and Methods

From bovine incisors, 143 specimens were prepared, embedded in epoxy resin and polished. The specimens were partially covered with nail varnish (control), and the resulting four windows were demineralised for 50 days (pH 4.95, 37° C.). After demineralisation, three of the four windows were etched with phosphoric acid (37° C.) for 5 seconds. Each of the 12 experimental materials (N° 13-21 and 4-6; Table 2 as well as the adhesive were applied onto the lesions (n=11). After removing excessive material, the resins were light cured for 30 seconds. Specimens were cut perpendicularly to their surfaces and thin sections were studied using confocal microscopy (CLSM) as well as microradiography (TMR)

2. Results

Mean lesion depths (SD) observed with CLSM [299 (57) µm] and TMR [296 (51) µm] were comparable. Compared to the adhesive, the PQs were significantly increased for the three infiltrants based on TEGDMA (N° 4-6; Table 2 as well as for those containing BisGMA and TEGDMA (25:75) and ethanol (N° 20, 21) (p<0.05; ANOVA). FIG. 5 shows penetration quotients (FIG. 5A) and absolute penetration depths (FIG. 5B) of the various materials.

FIG. 6 shows the correlation between the penetration depth and the square root of the product of the PC and the application time ($r^2$=0.847). The good correlation indicates that the Washburn equation is capable to describe the penetration of infiltrants into enamel lesions. Therefore, the PC appears to be a suitable predictor for the ability of an infiltrant to penetrate enamel lesions rapidly. Infiltrants should have high penetration coefficients (>50 cm/s) to achieve rapid infiltration of enamel lesions.

Example 5

Influence of PC on Lesion Progression of Infiltrated Enamel Lesions Under Demineralising Conditions The aim of this study was to evaluate the progression of sealed artificial enamel lesions under demineralizing conditions.

1. Materials and Methods

In each of 130 bovine enamel specimens, four caries like lesions were created (demineralising solution pH 4.95; 50 days). In each specimen, three lesions were etched with phosphoric acid gel for 5 seconds, whereas one lesion remained untreated. Each of 12 experimental composites (N° 13-21 and 4-6; Table 2) showing different PCs as well as the adhesive Excite were applied onto the lesions (n=10). After removing excessive material, the resins were light cured for 30 seconds. Subsequently, specimens were cut perpendicular to the surface. Half of each specimen was used as baseline control. The other half was exposed to the demineralization solution for further 50 days (effect). Specimens were observed using confocal microscopy.

2. Results

During the second demineralization period, mean lesion depth (SD) progressed from 299 (51) µm to 418 (76) µm (41.5%). Infiltrated lesions showed significantly reduced lesion progression compared to untreated controls (p>0.001; t-test). For Excite® (PC 32 31.3 cm/s) as well as for infiltrants having a PC<100 cm/s, a significant progression of lesion depth could be shown (FIG. 6). Infiltrants with higher PCs showed no significant progression (p>0.05). A negative correlation between the progression of sealed lesions and the square root of the product of PC and penetration time could be found ($r^2$=0.625; p<0.01; FIG. 8). It can be concluded that infiltrants with high PCs are more suitable to inhibit lesion progression compared to those with lower PCs.

Example 6

Method of Infiltrating Enamel

1. Materials

Means useful for carrying out the method of infiltrating enamel comprise a separating means (FIG. 9) for separating the teeth in situ, application strips (FIG. 10A) for applying the conditioner, e.g. hydrochlorid acid gel, an infiltrant and, optionally, a higher viscous light curing mixture of monomers, and cleaning strips (FIG. 10B).

The separating means is shaped like a wedge having a trapezoid cross sectional area (FIG. 9), and is made of solid material such as methacrylate or wood. The measurements are, for example, approximately 12 mm in length and up to approximately 2,5 mm in width.

Both the application strips 1 to 3 (FIG. 10A) and the cleaning strips 4 (FIG. 10B) are based on a supporting polymer film having a thickness of up to approximately 100 µm. The application strips are of approximately 20 cm in length and 0.4 cm in width. They further comprise a delivery pad having a thickness of up to approximately 300 µm laminated onto the supporting polymer film. The delivery pad may be located more or less centrally on the strip, or may be located near one of the ends. The delivery pad is made of an absorbent material such as foam, felt or paper. The absorbent material is soaked with either hydrochloric acid gel, infiltrant or a higher viscous light curing mixture of monomers. The delivery pads may be soaked prior to use from appropriate stocks by the user, e.g. a dentist or a patient. Alternatively, the application strips are in form of ready-to-use strips, i.e. they are commercially available with pre-soaked delivery pads and are preferably vacuum-packed or otherwise protected, e.g. from humidity.

A cleaning strip is of approximately 20 cm in length and 0.7 cm in width and comprises a region of approximately 2 cm in width having several laps, e.g. four laps, made of silicone or rubber. The laps are adapted, e.g. by choice of the material, to be flexible and to serve cleaning purposes between two adjacent teeth. It is preferred that two laps form a type of cavity for taking up a fluid or other material. As shown in FIG. 10B, the laps preferably are at an oblique position. The region where the laps are arranged may be located more or less centrally on the strip, or may be located near one of the ends.

The means useful for carrying out the method of infiltrating enamel as described above may be commercially available in the form of a kit.

In one embodiment, such a kit, preferably to be used by a patient, comprises the following:
(a) at least one ready-to-use application strip having a delivery pad soaked with hydrochlorid acid gel;
(b) at least one ready-to-use application strip having a delivery pad soaked with an infiltrant;
(c) optionally at least one ready-to-use application strip having a delivery pad soaked with a higher viscous light curing mixture of monomers; and
(d) at least one cleaning strip.

In another embodiment, such a kit comprises the following:
(a) at least one application strip having a delivery pad to be soaked with hydrochlorid acid gel;
(b) at least one application strip having a delivery pad to be soaked with an infiltrant;
(c) optionally at least one application strip having a delivery pad to be soaked with a higher viscous light curing mixture of monomers;
(d) at least one cleaning strip;
(e) hydrochloric acid gel;
(f) infiltrant; and
(g) optionally higher viscous light curing mixture of monomers.

The hydrochloric acid in (e), the infiltrant in (f), and the higher viscous light curing mixture of monomers in (g) may be stored in a container, e.g. a bottle, as a stock or, alternatively, may be stored in single-use-packages.

Both kit may additionally comprise a separating means.

2. Procedure for Carrying out the Method Using Ready-To-Use Application Strips

According to common practice of a dentist, a dental dam is applied in order to dry up the operation area, and the separating means is used to separate the teeth by about 300 μm. In case that the method is used by a patient, drying up the operation area may be disposable.

In a first step, a strip comprising a delivery pad soaked with hydrochloric acid gel is used for applying hydrochloric acid to an area of a tooth to be treated. For that purpose, the strip is introduced from occlusal or from lingual/palatinal direction into the region between the tooth to be treated and the adjacent tooth. While introducing the strip, it is directed such that the upper surface of the delivery pad faces the approximal surface of the tooth to be treated. Then, the delivery pad is thoroughly placed in a c-shaped manner at the approximal area to be treated, and the delivery pad is pressed to the tooth's surface. After a residence time of about 2 min, excessive hydrochloric acid gel adhered to the surface of the tooth is rinsed, and the treated area is air dried or is dried using ethanol and/or acetone.

In a second step, the strip comprising a delivery pad soaked with infiltrant is used in a similar manner as the strip in the first step.

In a third step, the cleaning strip is used in order to remove excess of infiltrant. After having introduced the cleaning strip into the area between the tooth to be treated and the adjacent tooth, the strip is moved from lingual/palatinal to vestibular direction. The movement of the strip may be bi-directionally for several times until the cavities formed by the flexible laps are filled with infiltrant.

In a fourth step, the infiltrant having infiltrated the enamel lesion is light cured.

In a fifth step, the strip comprising a delivery pad soaked with either an infiltrant or a higher viscous light curing mixture of monomers is used in a similar manner as the strips in the first and second steps.

Optionally, a further cleaning strip is used as described above in the third step in order to remove excess of material applied in the last step, e.g. the mixture of monomers.

In a further step, the monomers are polymerized by light. The final layer produced by light curing the higher viscous mixture of monomers allows for a sealing of the treated area, and thus for enhanced resistance of the infiltrated enamel.

Finally, the dental dam, if used, is removed from the operation area.

The invention claimed is:

1. A kit for infiltrating enamel lesions, comprising two components, comprising:
   (a) as a gel component, a conditioner comprising 1-30% hydrochloric acid, wherein said conditioner is a hydrochloric acid gel comprising about 1-30% (w/w) of hydrochloric acid; and
   (b) as a liquid component, a light-curing or self-curing infiltrant, said infiltrant comprising a low viscous light curing liquid resin and an additive for curing,
   wherein the liquid component has a penetration coefficient of >50 cm/s.

2. The kit according to claim 1, further comprising:
   (c) a higher viscous light curing mixture of monomers.

3. The kit according to claim 1, wherein the infiltrant (b) has a penetration coefficient of >50 cm/s or comprising a low viscous light curing resin having a penetration coefficient of >50 cm/s according to the following equation:

$$PC = \left(\frac{\gamma \cdot \cos\theta}{2\eta}\right) \quad \text{-Equation 2-}$$

wherein:
PC refers to the penetration coefficient;
γ refers to the surface tension of the liquid resin (to air);
θ refers to the contact angle of the liquid resin (to enamel); and
η refers to dynamic viscosity of the liquid resin.

4. The kit according to claim 1, further comprising at least one application strip and/or at least one cleaning strip and/or a separating means.

5. A kit for infiltrating enamel, comprising:
   (a) a first application strip comprising a conditioner comprising 1-30% hydrochloric acid;
   (b) a second application strip comprising a light-curing or self-curing infiltrant, said infiltrant comprising a low viscous light curing liquid resin and an additive for curing, wherein the infiltrant has a penetration coefficient of >50 cm/s; and
   (c) at least one cleaning strip.

6. The kit according to claim 5, additionally comprising:
   (d) an application strip comprising a higher viscous light curing mixture of monomers.

7. The kit according to claim 5, additionally comprising:
   (e) a separating means.

8. The kit according to claim 5, wherein the conditioner (a) is a hydrochloric acid gel comprising about 1-30% (w/w) of hydrochloric acid.

9. The kit according to claim 5, wherein the infiltrant (b) has a penetration coefficient of >50 cm/s or comprising a low viscous light curing resin having a penetration coefficient of >50 cm/s according to the following equation:

$$PC = \left(\frac{\gamma \cdot \cos\theta}{2\eta}\right) \quad \text{-Equation 2-}$$

wherein:
PC refers to the penetration coefficient;
γ refers to the surface tension of the liquid resin (to air);
θ refers to the contact angle of the liquid resin (to enamel); and
η refers to dynamic viscosity of the liquid resin.

10. The kit according to claim 5, wherein said infiltrant (b) comprises at least one resin selected from the group comprising dental composite resins, dental adhesive resins and fissure sealant resins.

11. The kit according to claim 5, wherein the infiltrant (b) comprises at least one resin or low viscous resin selected from the group comprising bis-GMA, 2,2-bis[4-(2-hydroxy-3-methacryloxypropoxy)phenyl] propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate; wherein the infiltrant has a penetration coefficient of >50 cm/s or comprising a low viscous light curing resin having a penetration coefficient of >50 cm/s.

12. The kit according to claim 5, wherein in the infiltrant (b) the additive for curing is selected from the group comprising CQ, camphoroquinone; BL, benzil; DMBZ, dimethoxy-benzoin; CEMA, N-(2-cyanoethyl)N-methylanilin; DMA-BEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxy-ethylamine; HMBP, 2-hydroxy-4-methoxy benzophenone; TINP, 2(2'-hydroxy-5'-methylphenyl) benzotriazol; 2-(5-chloro-2H-benzotriazole-2-yl)-6-(1,1-dimethylethyl)-4-methyl-phenol (CAS Registry Number 3896-11-5); 2-(2'-hydroxy-3'-s-butyl-5'-butyl-phenyl)benzotriazole (CAS Registry Number 36437-37-3); 2-(2H-benzotriazol-2-yl)-4,6-ditertpentylphenol (CAS Registry Number 25973-55-1); HQME, hydroxyquinone monomethyl ester; BHT 2,6-di-t-butyl-4-methyl phenol; MBP 2,2-methylene-bis(6-t-butylphenol); MBEP, 2,2-Methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

13. The kit according to claim 5, wherein the additive for curing is selected from the group comprising organic acids or salts thereof.

14. The kit according to claim 13, wherein the organic acid is selected from the group comprising alkane sulfinic acids, alicyclic sulfinic acids, and aromatic sulfinic acids.

15. The kit according to claim 14, wherein the alkane sulfinic acid is selected from the group comprising ethane sulfinic acid, propane sulfinic acid, hexane sulfinic acid, octane sulfinic acid, decane sulfinic acid, and dodecane sulfinic acid; the alicyclic sulfinic acid is cyclohexane or cyclooctane sulfinic acid; the aromatic sulfinic acid is selected from the group comprising benzene sulfinic acid, o-toluene sulfinic acid, p-toluene sulfinic acid, ethylbenzene sulfinic acid, decylbenzene sulfinic acid, dodecylbenzene sulfinic acid, chlorobenzene sulfinic acid, and naphthalene sulfinic acid.

16. The kit according to claim 13, wherein the organic acid is selected from the group comprising 1,3,5-trimethyl barbituric acid, 1,3,5-triethylbarbituric acid, 1,3- dimethyl-5-ethyl barbituric acid, 1,5-dimethyl barbituric acid, 1-methyl-5-ethyl barbituric acid, 1-methyl-5-propyl barbituric acid, 5-ethyl barbituric acid, 5-propyl barbituric acid, 5-butyl barbituric acid, 5-methyl-1-butyl barbituric acid, 1-benzyl-5-phenyl barbituric acid, and 1-cyclohexyl-5-ethyl barbituric acid.

17. The kit according to claim 5, wherein the additive for curing is selected from the group comprising persulfates and organic peroxides.

18. The kit according to claim 17, wherein the organic peroxide is selected from the group comprising diacetyl peroxide, dipropyl peroxide, dibutyl peroxide, dicapryl peroxide, dilauryl peroxide, dibenzoyl peroxide, p,p'-dichloro benzoyl peroxide, p,p'- dimethy oxybenzoyl peroxide, p,p'-dimethyl benzoyl peroxide, and p,p'-dinitro benzoyl peroxide.

19. The kit according to claim 5, wherein the low viscous resin comprises 22% bis-GMA, 2,2-bis[4-(2-hydroxy-3-methacryloxypropoxy)phenyl]propane; 67% TEGDMA, triethylene glycol dimethacrylate; 10% ethanol; 0.5% DABE, ethyl 4-(dimethylamino)benzoate, and 0.5% camphorquinone.

20. The kit according to claim 8, wherein said gel comprises 5-15% (w/w) of hydrochloric acid.

21. The kit according to claim 13, wherein said additive for curing is selected from the group comprising sulfinic acids, barbituric acids, and barbituric acid derivatives.

* * * * *